US009249471B2

(12) United States Patent
Erridge

(10) Patent No.: US 9,249,471 B2
(45) Date of Patent: Feb. 2, 2016

(54) ASSAY FOR MEASURING INFLAMMATORY MOLECULES IN ORALLY INGESTIBLE SAMPLES

(75) Inventor: Clett Ben Erridge, Leicestershire (GB)

(73) Assignee: UNIVERSITY OF LEICESTER, Leicestershire (GB)

( * ) Notice: Subject to any disclaimer, the term of this patent is extended or adjusted under 35 U.S.C. 154(b) by 23 days.

(21) Appl. No.: 13/704,182

(22) PCT Filed: Jun. 9, 2011

(86) PCT No.: PCT/GB2011/051075
§ 371 (c)(1),
(2), (4) Date: Dec. 13, 2012

(87) PCT Pub. No.: WO2011/158016
PCT Pub. Date: Dec. 22, 2011

(65) Prior Publication Data
US 2013/0095094 A1    Apr. 18, 2013

(30) Foreign Application Priority Data

Jun. 15, 2010 (GB) .................................. 1009985.1
Dec. 22, 2010 (GB) .................................. 1021711.5

(51) Int. Cl.
*G01N 33/53* (2006.01)
*G01N 33/68* (2006.01)
*G01N 33/569* (2006.01)
*C12Q 1/68* (2006.01)
*A61K 31/665* (2006.01)
*A61K 31/7105* (2006.01)
*A61K 38/16* (2006.01)
*G01N 33/566* (2006.01)
*G01N 33/554* (2006.01)
*A61K 39/395* (2006.01)

(52) U.S. Cl.
CPC ............ *C12Q 1/6897* (2013.01); *A61K 31/665* (2013.01); *A61K 31/7105* (2013.01); *A61K 38/164* (2013.01); *G01N 33/566* (2013.01); *G01N 33/569* (2013.01); *G01N 33/6893* (2013.01); *G01N 2500/00* (2013.01); *G01N 2800/02* (2013.01); *G01N 2800/18* (2013.01); *G01N 2800/50* (2013.01); *G01N 2800/52* (2013.01)

(58) Field of Classification Search
None
See application file for complete search history.

(56) References Cited

FOREIGN PATENT DOCUMENTS

WO    WO 02/085933 A1    10/2002
WO    WO 2009/115533 A1   9/2009
WO    WO 2011/158016 A2   12/2011

OTHER PUBLICATIONS

Beck et al., Relationship of periodontal disease to carotid artery intima-media wall thickness: the atherosclerosis risk in communities (ARIC) study. *Arterioscler Thromb Vasc Biol* (2001) 21:1816-1822.
Coats et al., *Porphyromonas gingivalis* lipopolysaccharide antagonizes *Escherichia coli* lipopolysaccharide at Toll-like receptor 4 in human endothelial cells. *Infect Immun* (2003) 71:6799-6807.
Copeland et al., Inflammation and the host response to injury investigators. Acute inflammatory response to endotoxin in mice and humans. *Clin Diagn Lab Immunol* (2005) 12:60-67.
Delahooke et al., Tumor necrosis factor induction by an aqueous phenol-extracted lipopolysaccharide complex from *Bacteroides* species. *Infect Immun* (1995) 63:840-846.
Erridge et al., The induction of colitis and ileitis in mice is associated with marked increases in intestinal concentrations of stimulants of TLRs 2, 4, and 5. *PLoS One* (2010) 5:e9125.
Erridge et al., Saturated fatty acids do not directly stimulate Toll-like receptor signalling. *Arterioscler Thromb Vasc Biol* (2009) 29:1944-1949.
Erridge et al., Non-enterobacterial endotoxins stimulate human coronary artery but not venous endothelial cell activation via Toll-like receptor 2. *Cardiovascular Research* (2007) 73:181-189.
Erridge et al., Oxidised phospholipid inhibition of Toll-like receptor (TLR) signalling is restricted to TLR2 and TLR4—roles for CD14, LPS-binding protein and MD2 as targets for specificity of inhibition. *J Biol Chem* (2008) 283:24748-24759.
Erridge, The roles of Toll-like receptors in atherosclerosis. *J Innate Immun* (2009) 1:340-349.
Erridge, The capacity of foodstuffs to induce innate immune activation of human monocytes in vitro is dependent on food content of stimulants of Toll-like receptors 2 and 4. *Br J Nutr* (2010) 20:1-9.
Erridge, Stimulants of Toll-like receptor (TLR)-2 and TLR-4 are abundant in certain minimally-processed vegetables. *Food Chem Toxicol* (2011) 49:1464-1467.
Erridge, Accumulation of stimulants of Toll-like receptor (TLR)-2 and TLR4 in meat products stored at 5 degrees C. *J Food Sci* (2011) 2:H72-79.
Ghoshal et al., Chylomicrons promote intestinal absorption of lipopolysaccharides. *J Lipid Res* (2009) 50:90-97.
Hirschfeld et al., Cutting edge: repurification of lipopolysaccharide eliminates signaling through both human and murine toll-like receptor 2. *J Immunol* (2000) 165:618-622.
Kikkert et al., Activation of toll-like receptors 2 and 4 by gram-negative periodontal bacteria. *Oral Microbiol Immunol* (2007) 22:145-151.
Kumar et al., Toll-like receptors and innate immunity. *Biochem Biophys Res Commun* (2009) 388:621-625.
Lappin et al., Stimulants of Toll-like receptors 2 and 4 are elevated in saliva of periodontitis patients compared with healthy subjects. *J Clin Periodontol* (2011) 38(4):318-325.
Leenstra et al., Oral endotoxin in healthy adults. *Oral Surg Oral Med Oral Pathol Oral Radiol Endod* (1996) 82:637-643.

(Continued)

*Primary Examiner* — Bridget E Bunner
*Assistant Examiner* — Fozia Hamud
(74) *Attorney, Agent, or Firm* — Squire Patton Boggs (US) LLP

(57)                ABSTRACT

The invention provides assays and apparatuses for assessing the ability of certain orally-ingestible samples, such as saliva or foodstuffs to cause inflammation, and thus the health risk such samples can cause upon ingestion by a subject. The invention also provides an assay to monitor an individual's diet with regards to inflammation risk. The invention also extends to methods of preventing inflammatory diseases.

9 Claims, 11 Drawing Sheets

(56) References Cited

OTHER PUBLICATIONS

Mager et al, Effects of periodontitis and smoking on the microbiota of oral mucous membranes and saliva in systemically healthy subjects. *J Clin Periodontol* (2003) 30:1031-1037.

Gómez et al., Tongue coating and salivary bacterial counts in healthy/gingivitis subjects and periodontitis patients. *J Clin Periodontol* (2001) 28:970-978.

Teeuw et al., Effect of periodontal treatment on glycemic control of diabetic patients: a systematic review and meta-analysis. *Diabetes Care* (2010) 33:421-427.

Tonetti, Effect of periodontal treatment on glycemic control of diabetic patients: a systematic review and meta-analysis. *J Clin Periodontol* (2009) 36 Suppl 10:15-19.

Yoshimura et al., Lipopolysaccharides from periodontopathic bacteria *Porphyromonas gingivalis* and *Capnocytophaga ochracea* are antagonists for human toll-like receptor 4. *Infect Immun* (2002) 70:218-225.

IPRP and Written Opinion in PCTGB2011051075, issued Feb. 26, 2013.

Erridge, "Diet, commensals and the intestine as sources of pathogen-associated molecular patterns in atherosclerosis, type 2 diabetes and non-alcoholic fatty liver disease", *Atherosclerosis* (2011) 216:1-6.

Erridge, "Vascular cell responsiveness to Toll-like receptor ligands in carotid atheroma", *European Journal of Clinical Investigation* (2008) 38:713-720.

Huang et al.,"Use of Toll-Like Receptor Assays to Detect and Identify Microbial Conaminants in Biological Products", *Journal of Clinical Microbiology* (2009) 47:3427-3434.

Al-Attas et al., Changes in endotoxin levels in T2DM subjects on anti-diabetic therapies (2009) *Cardiovascular Diabetology* 8:20, 10 pages.

Arkan et al., IKK-β links inflammation to obesity-induced insulin resistance (2005) *Nature Medicine* 11:191-198.

Balasa et al., A Mechanism for IL-10-Mediated Diabetes in the Nonobese Diabetic (NOD) Mouse: ICAM-1 Deficiency Blocks Accelerated Diabetes[1,2] (2000) *The Journal of Immunology* 165:7330-7337.

Belew et al., Endotoxemia in Psoriasis (1982) *Arch Dermatol* 118:142-143.

Brånén et al., Inhibition of Tumor Necrosis Factor-α Reduces Atherosclerosis in Apolipoprotein E Knockout Mice (2004) *Arterioscler Thromb Vasc Biol* 24:2137-2142.

Busch et al., Determination of endotoxin in inflammatory rheumatic diseases—the effect of nonsteroidal anti-inflammatory agents on intestinal permeability (1988) *Z Rheumatol* 47:156-60 [abstract only].

Cani et al., Metabolic Endotoxemia Initiates Obesity and Insulin Resistance (2007) *Diabetes* 56:1761-1772.

Collins et al., P-Selectin or Intercellular Adhesion Molecule (ICAM)-1 Deficiency Substantially Protects against Atherosclerosis in Apolipoprotein E-deficient Mice (2000) *J. Exp. Med.* 191:189-194.

Danilenko, D.M., Review Paper: Preclinical Models of Psoriasis (2008) *Vet Pathol* 45:563-575.

Dansky et al., Adhesion of Monocytes to Arterial Endothelium and Initiation of Atherosclerosis Are Critically Dependent on Vascular Cell Adhesion Molecule-1 Gene Dosage (2001) *Arterioscler Thromb Vasc Biol* 21:1662-1667.

Elsenberg et al., Increased cytokine response after toll-like receptor stimulation in patients with stable coronary artery disease (2013) *Atherosclerosis* 231:346-351.

Gareus et al., Endothelial Cell-Specific NF-κB Inhibition Protects Mice from Atherosclerosis (2008) *Cell Metabolism* 8:372-383.

Ghoshal et al., Chylomicrons promote intestinal absorption of lipopolysaccharides (2009) *Journal of Lipid Research* 50:90-97.

Harte et al., Elevated endotoxin levels in non-alcoholic fatty liver disease (2010) *Journal of Inflammation* 7:15, 10 pages.

Heimesaat et al., Exacerbation of murine ileitis by Toll-like receptor 4 mediated sensing of lipopolysaccharide from commensal *Escherichia coli* (2007) *Gut* 56:941-948.

Hotta et al., Lipopolysaccharide-induced Colitis in Rabbits (1986) *Res Exp Med* 186:61-69.

Johansson et al., Innate immune receptor NOD2 promotes vascular inflammation and formation of lipidrich necrotic cores in hypercholesterolemic mice (2014) *European Journal of Immunology*, 32 pages, doi: 10.1002/eji.201444755 (article accepted, not yet published).

Krogh-Madsen et al., Effect of short-term intralipid infusion on the immune response during low-dose endotoxemia in humans (2008) *Am J Physiol Endocrinol Metab* 294:E371-E379.

Lee et al., Essential roles of Toll-like receptor-4 signaling in arthritis induced by type II collagen antibody and LPS (2005) *International Immunology* 17:325-333.

Leinonen et al., Insulin resistance and adiposity correlate with acute-phase reaction and soluble cell adhesion molecules in type 2 diabetes (2003) *Atherosclerosis* 166:387-394.

Liu et al., *Porphyromonas gingivalis* and *E. coli* Lipopolysaccharide Exhibit Different Systemic but Similar Local Induction of Inflammatory Markers (2008) *J Periodontol* 79:1241-1247.

Miller et al., Endotoxin and metabolic syndrome (2009) *Atherosclerosis* doi:10.1016/j.atherosclerosis.2009.03.049, 1 page.

Mullick et al., Modulation of atherosclerosis in mice by Toll-like receptor 2 (2005) *J. Clin. Invest.* doi:10.1172/JC125482, 8 pages.

Rojo et al., Serum Lipopolysaccharide-Binding Protein in Endotoxemic Patients with Inflammatory Bowel Disease (2007) *Inflamm Bowel Dis* 13:269-277.

Schultz et al., Effects of Inhibition of Interleukin-6 Signalling on Insulin Sensitivity and Lipoprotein (A) Levels in Human Subjects with Rheumatoid Diseases (2010) *PloS One* 5:e14328, 7 pages.

Swerdlow D.I., The interleukin-6 receptor as a target for prevention of coronary heart disease: a mendelian randomisation analysis (2012) *Lancet* 379:1214-1224.

Tomofuji et al., Chronic Administration of Lipopolysaccharide and Proteases Induces Periodontal Inflammation and Hepatic Steatosis in Rats (2007) *J Periodontol* 78:1999-2006.

Ventre et al., Targeted Disruption of the Tumor Necrosis Factor-α Gene (1997) *Diabetes* 46:1526-1531.

Wang et al., Peptidoglycan primes for LPS-induced release of proinflammatory cytokines in whole human blood (2001) *Shock* 16:178-182.

Westertep et al., Apolipoprotein C-I Is Crucially Involved in Lipopolysaccharide-Induced Atherosclerosis Development in Apolipoprotein E—Knockout Mice (2007) *Circulation* 116:2173-2181.

Wiedermann et al., Association of Endotoxemia With Carotid Atherosclerosis and Cardiovascular Disease (1999) *J Am Coll Cardiol* 34:1975-1981.

Cell-Specific Transfection Protocols, *Life Technologies*, https://www.lifetechnologies.com/us/en/home/life-science/cell-culture/transfection/transfection-support/transfection-selection-tool-html, Thermo Fisher Scientific (2015), printed Apr. 20, 2015, 14 pages.

General Transfection Protocols, *Life Technologies*, https://www.lifetechnologies.com/us/en/home/life-science/cell-culture/transfection/transfection-support-plasmid-transfection.html, Thermo Fisher Scientific (2015), printed Apr. 20, 2015, 3 pages.

Guan et al., Identification of Novel Synthetic Toll-like Receptor 2 Agonists by High Throughput Screening (2010) *The Journal of Biological Chemistry* 285:23755-23762.

(Biological activity relative to Pam$_3$CSK$_4$)

ASSAY FOR MEASURING INFLAMMATORY MOLECULES IN ORALLY INGESTIBLE SAMPLES

This application is the National Stage of International Application No. PCT/GB2011/051075, filed Jun. 9, 2011, which claims priority to United Kingdom application No. 1009985.1, filed Jun. 15, 2010, and to United Kingdom application No. 1021711.5, filed Dec. 22, 2010, each of which is hereby incorporated by reference in its entirety.

FIELD OF THE INVENTION

The invention relates to assays, and in particular to assays and apparatuses for assessing the ability of certain orally-ingestible samples, such as saliva or foodstuffs to cause inflammation, and thus the health risk such samples can cause upon ingestion by a subject. The invention also concerns an assay to monitor an individual's diet with regards to inflammation risk. The invention also extends to methods of preventing inflammatory diseases.

BACKGROUND

Dietary factors have long been understood to play a critical role in the development of diseases, such as atherosclerosis and insulin resistance. As recent evidence indicates that chronic inflammatory processes also underpin the development of these diseases, current research focuses on the potential mechanisms that link nutrition and inflammatory signalling. It has been shown that the ingestion of fatty meals is associated with the transient activation of circulating monocytes and increases in circulating inflammatory markers, such as TNF-α and IL-6. These responses have been found to be due to the induction of mild post-prandial endotoxaemia following a fatty meal in human subjects and in animal models. Not only endotoxin (also referred to as lipopolysaccharide, LPS), but also bacterial lipopeptides (BLP) and other circulating pathogen-associated molecular patterns (PAMPs) may promote inflammation observed in the post-prandial phase.

PAMPs are recognised by pattern recognition receptors in plants and mammals. Some PAMPs are recognised by Toll-like receptors (TLRs). TLRs are a family of receptors known to elicit innate immune activation of mammalian monocytes. Each member of the TLR family recognises its specific repertoire of ligands. For example, TLR-4 recognises LPS, whereas TLR-2 recognises BLP, and so on. Some PAMPS are recognised by nucleotide-binding oligomerisation domain (NOD)-like receptors (NLR), such as NOD1 and NOD2.

To date, it has been widely considered that the source of the circulating endotoxins thought to cause postprandial inflammation (i.e. after eating a meal) is the resident intestinal microflora in the mammal. It has been recently discovered that the likely site of diet-induced LPS translocation is at the small intestine. However, the small intestine contains only very low levels of endogenous bacteria. Furthermore, recent findings suggest that chylomicrons are the likely vehicle for endotoxin translocation in response to a fatty meal.

The inventor has reconsidered the conventional understanding of the sources of endotoxins which are thought to cause inflammation, and investigated whether common foodstuffs may contain appreciable quantities of endotoxins, or other agents, such as Toll-like receptor (TLR) stimulants or nucleotide-binding oligomerisation domain (NOD)-like receptor (NLR) stimulants, that may be capable of eliciting innate immune activation of human monocytes. However, measurement of the concentrations of TLR-stimulants or NLR-stimulants in food products presents several difficulties. For example, as TLR-stimulants or NLR stimulants can be derived from any type of micro-organism, they show an inherently large antigenic and molecular diversity, which precludes the use of traditional ELISA or mass-spectrometry techniques. The most widely used assay for the detection of endotoxins in foodstuffs is the limulus-amoebocyte-lysate (LAL) assay. However, the inventor has found that the LAL assay is not suitable for measuring the quantities of endotoxins, Toll-like receptors (TLRs) stimulants or NOD-like receptor (NLR) stimulants for several reasons.

Firstly, it is well-established that the limulus assay generates a positive reaction to β-glucans which can be common in foodstuffs, thereby potentially generating false-positive results. Secondly, the inventor has found that several forms of non-enterobacterial lipid-A, which can often be antagonists of TLR-4 and LPS-signalling in human cells, stimulate a positive reaction in the limulus assay. Notably, many environmental and food-borne organisms possess a non-enterobacterial lipid-A structure which does not stimulate human TLR-4/MD2. Thirdly, as the LAL assay is insensitive to lipopeptides and flagellins, it cannot be used to quantify these PAMPs.

It will therefore be appreciated that there are a number of problems associated with currently available assays for detecting the inflammatory risk posed by foodstuffs. Accordingly, there is a need for improved assays, which accurately, rapidly and conveniently assess the inflammatory risk of foodstuffs. In addition, to determining the inflammatory risk of foodstuffs, there is also a need for improved assays which assess the inflammatory risk caused by saliva, and other orally-ingestible samples. Accordingly, the inventor set out to develop an assay for determining the risk of orally-ingestible biological samples, such as saliva or foodstuffs, for causing inflammation.

SUMMARY

Hence, according to a first aspect of the invention, there is provided an assay for determining the risk of an orally-ingestible biological sample for causing inflammation, the assay comprising analysing the concentration of a Toll-like receptor (TLR) stimulant or a nucleotide-binding oligomerisation domain (NOD)-like receptor (NLR) stimulant in an orally-ingestible biological sample and comparing this concentration with a reference concentration of TLR-stimulant or NLR-stimulant known to represent an inflammation risk, wherein an increased concentration of TLR-stimulant or NLR-stimulant in the sample compared to the reference concentration indicates that the sample causes inflammation.

In a second aspect of the invention, there is provided an apparatus for determining the risk of an orally-ingestible biological sample for causing inflammation, the apparatus comprising:
(i) means for determining the concentration of a Toll-like receptor (TLR) stimulant or a nucleotide-binding oligomerisation domain (NOD)-like receptor (NLR) stimulant in an orally-ingestible biological sample; and
(ii) a reference corresponding to the concentration of a TLR-stimulant or NLR-stimulant known to represent an inflammation risk, wherein the apparatus is used to identify an increased concentration of a TLR-stimulant or a NLR-stimulant in the sample, thereby suggesting that the sample causes inflammation.

BRIEF DESCRIPTION OF FIGURES

For a better understanding of the invention and to show how embodiments of the same may be carried into effect, reference will now be made, by way of example, to the accompanying drawings, in which.

Figure 14:
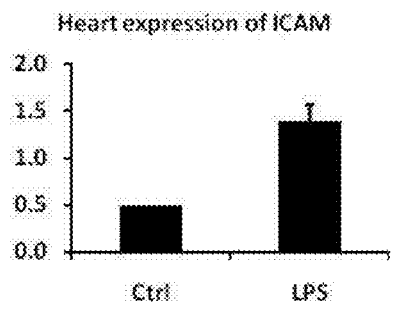
Figure 15:
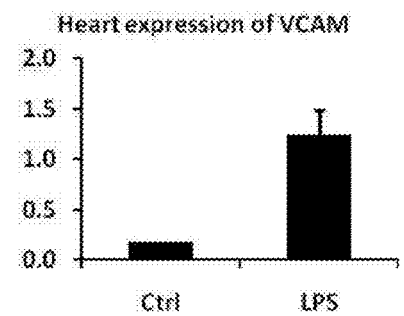

FIG. 14 is a graph showing the expression of ICAM-1 in mouse heart 48 hours after oral LPS challenge; and FIG. 15 is a graph showing the expression of VCAM-1 in mouse heart 48 hours after oral LPS challenge.

DETAILED DESCRIPTION OF PREFERRED EMBODIMENTS

Using the assay and the apparatus (which may be a kit) of the invention, the inventor tested a wide range of common foodstuffs (see FIGS. 1-3) and saliva (see FIGS. 8-13) to determine if they contain appreciable quantities of endotoxins, or other similar agents that may be capable of eliciting innate immune activation of human monocytes, i.e. TLR stimulants or NLR stimulants. The inventor was surprised to identify the presence of inflammatory stimulants at levels of biological significance in many of the foodstuffs and saliva samples that were tested. These contaminants are believed to be of pathological relevance in the context of common chronic inflammatory diseases, such as atherosclerosis, insulin resistance, arthritis, periodontitis, diabetes and cardiovascular disease. Thus, the inventor found that Toll-like receptor (TLR) stimulants and NOD-like receptor (NLR) stimulants are present in the biological sample (e.g. from the foodstuff or saliva) at a concentration which is indicative of inflammation risk.

Accordingly, the assay and apparatus of the invention may be used to detect chronic inflammatory diseases, or metabolic or cardiovascular conditions or diseases, such as periodontitis, non-alcoholic fatty liver disease (NAFLD), atherosclerosis, coronary artery disease, metabolic syndrome, hyperinsulinaemia, insulin resistance, type 2 diabetes mellitus (T2DM), arthritis, psoriasis, Crohn's disease or ulcerative colitis.

The inventor has established a surprising link between food-borne or saliva pathogen associated molecular patterns (PAMPs), and the risk of inflammation or metabolic diseases that may be caused by these PAMPs. The assay and apparatus may or may not be used for detecting acute diseases, such as food poisoning, which may be caused by PAMPs. Thus, advantageously, the assay and apparatus of the invention can be used to detect PAMPs in foodstuffs even in the absence of food-poisoning bacteria.

Furthermore, the assay and apparatus of the invention do not require the use of antibodies to detect bacterial components, which would be very specific for particular species or strains of bacteria. Given that hundreds of different species may be present in any one sample, many of which may not be pro-inflammatory, antibodies could not be used to quantify them. Furthermore, antibodies cannot be used to quantify PAMPs because the portions of these molecules that are targeted by antibodies are too variable. Thus, only innate immune receptors (such as TLRs) have the binding sites necessary for interacting with the conserved domains of PAMPs.

Preferably, the apparatus of the second aspect is arranged to carry out the assay of the first aspect. The assay and the apparatus according to the invention do not suffer from the problems to which the LAL assay is prone, such as generating false positives. Furthermore, advantageously, the assay and the apparatus of the invention may be used to accurately and conveniently quantify TLR stimulants or NLR stimulants (i.e. PAMPs), thereby rapidly assessing the inflammation risk of the test orally-ingestible biological sample.

In one embodiment, the orally-ingestible biological sample may comprise saliva. In another embodiment, the orally-ingestible biological sample may comprise a foodstuff.

Thus, in another aspect, there is provided an assay for determining the risk of a foodstuff for causing inflammation, the assay comprising analysing the concentration of a Toll-like receptor (TLR) stimulant or a nucleotide-binding oligomerisation domain (NOD)-like receptor (NLR) stimulant in a sample from a test foodstuff and comparing this concentration with a reference concentration of TLR-stimulant or NLR-stimulant known to represent an inflammation risk, wherein an increased concentration of TLR-stimulant or NLR-stimulant in the sample from the test foodstuff compared to the reference concentration indicates that the foodstuff causes inflammation.

In yet another aspect, there is provided an apparatus for determining the risk of a foodstuff for causing inflammation, the apparatus comprising:
 (i) means for determining the concentration of a Toll-like receptor (TLR) stimulant or a nucleotide-binding oligomerisation domain (NOD)-like receptor (NLR) stimulant in a sample from a test foodstuff; and
 (ii) a reference corresponding to the concentration of a TLR-stimulant or NLR-stimulant known to represent an inflammation risk,
wherein the apparatus is used to identify an increased concentration of a TLR-stimulant or a NLR-stimulant in the sample from the test foodstuff, thereby suggesting that the foodstuff causes inflammation.

The skilled technician will appreciate what is meant by the term "Toll-like receptor" or "TLR", as used herein. There are 10 human TLRs, of which 9 are thought to be functional, and these receptors are known in the art (Erridge C. (2009) The roles of Toll-like receptors in atherosclerosis, J. Innate Immun. 1:340-349; and Kumar H, et al. (2009) Toll-like receptors and innate immunity, Biochem. Biophys. Res. Commun. 388:621-5). However, for the avoidance of doubt, TLRs are a class of pattern recognition receptors expressed by cells of the innate immune system that serve the purpose of detecting conserved molecules associated with microbial invasion, which are collectively referred to as pathogen associated molecular patterns (PAMPs).

The binding of PAMPs to their respective TLRs, either directly or indirectly via adaptor proteins, results in the dimerisation of TLRs which leads to the recruitment of specific intracellular signalling adaptors, such as myeloid differentiation primary response gene 88 (MyD88) and TIR-domain-containing adapter-inducing interferon-β (TRIF). These recruited adaptors are activated by the cytosolic domains of dimerised TLRs, leading to the activation of pro-inflammatory intracellular signalling pathways, such as NF-kB and p38 mitogen-activated protein kinase (MAPK) dependent pathways. The activation of these mediators by stimulated TLRs leads to the induction of inflammation, locally if PAMPs are present only in distinct tissues, or systemically if PAMPs are present in the blood. The inflammatory process initiated by TLR stimulation includes the expression of cytokines, chemokines and adhesion molecules which together promote the recruitment of monocytes and neutrophils into affected tissues.

The ligands of TLRs are referred herein as "TLR-stimulants" or "TLR agonists". The TLR-stimulant may stimulate any member of the Toll-like receptor family. TLR2 recognises bacterial lipopeptides by forming heterodimers with TLR1 or TLR6. TLR4 recognises enterobacterial lipid-A with the assistance of the accessory protein MD-2. TLR5 recognises bacterial flagellin and TLRs 3, 7, 8 and 9 serve to detect nucleic acid-based motifs.

In an embodiment of the invention, the TLR-stimulant may be a TLR-4 stimulant, a TLR-2 stimulant, a TLR-5 stimulant and/or a TLR-9 stimulant.

The skilled technician will appreciate what is meant by the term "nucleotide-binding oligomerisation domain (NOD)-like receptor" or "NLR", as used herein. NLRs are a family of cytoplasmic receptors that possess a nucleotide binding oligomerisation domain (NOD). The NLR family is also known as the CATERPILLER (CLR) or NOD-leucine rich repeat (LRR) family. NOD1 and NOD2 are family members of the NLR family. NOD1 or NOD2 stimulation results in the activation of both NF-κB and mitogen-activated protein kinase (MAPK) pathways.

The ligands of NLRs are referred herein as "NLR-stimulants" or "NLR agonists". NOD1 recognises a molecule called meso-diaminopimelic acid (meso-DAP), which is a peptidoglycan constituent of Gram negative bacteria. NOD2 proteins recognise intracellular muramyl dipeptide (MDP), which is a peptidoglycan constituent of both Gram positive and Gram negative bacteria.

In an embodiment of the invention, the NOD-like receptor (NLR) stimulant may stimulate any members of the NLR family. Preferably, the NLR stimulant may be a NOD1-stimulant and/or a NOD2-stimulant.

The skilled technician will appreciate that a TLR-stimulant or a NLR-stimulant is a positive modulator that is capable of altering the three-dimensional shape and configuration of the Toll-like receptor or NOD-like receptor from its inactive to active confirmation. Therefore, the TLR-stimulant or the NLR-stimulant may be capable of:

(i) altering the conformational state of the receptor, for example by stabilizing the active conformation of the receptor and/or maintaining the receptor in its active conformation to thereby allow the receptor to bind its natural ligand, e.g. LPS, BLP or peptidoglycan;
(ii) binding to the Toll-like receptor, and increasing, promoting or augmenting transmission at the receptor; and/or
(iii) promoting or activating the downstream signalling pathways activated by the TLR-stimulant or NLR-stimulant binding to the receptor.

It will be appreciated that each of mechanisms (i) to (iii) results in altering transmission at the receptor, and hence the activity thereof, to thereby activate the Toll-like receptor or NOD-like receptor.

The TLR-stimulant or the NLR-stimulant, the concentration of which is determined in the assays of the invention or using the apparatus of the invention, may be a pathogen-associated molecular pattern (PAMP) or a microbe-associated molecular pattern (MAMP). It will be appreciated that PAMPs or MAMPs are substances which are detected by the innate immune system, such as via Toll-like receptors (TLRs) or NOD-like receptors (NLRB), and elicit an immune response in plants and mammals.

Examples of suitable PAMPs, which may be detected by the assay and apparatus of the invention, may include a lipopolysaccharide (LPS), a bacterial lipopeptide (BLP), a flagellin, unmethylated CG-containing DNA (e.g. CpG motif-containing, bacterial DNA) or a bacterial peptidoglycan.

Suitable lipopolysaccharides (LPS) may include, but are not limited to, those that are derived from enterobacterial species, pseudomonads species, *acinetobacter* species or *erwinia* species. LPS may be recognised by CD14, TLR-4, and MD2. Therefore, LPS may be TLR-4 stimulants.

Suitable bacterial lipopeptides (BLP) may include, but are not limited to, di-acyl-lipopeptides derived from spirochetes or *mycoplasma* species, or tri-acyl lipopeptides derived from Gram-positive and Gram-negative bacteria. BLPs can be recognised by TLR-2, and, hence, may be TLR-2 stimulants.

Suitable flagellins may include, but are not limited to, those that may be expressed by any motile bacteria, such as enterobacterial species, for example *Salmonella typhimurium*, or pseudomonads such as *Pseudomonas putida*. Flagellins can be recognised by TLR-5, and hence, may be TLR-5 stimulants.

Bacterial genomic DNA is an immunostimulant and may be recognised by TLR9 (i.e. a TLR-9 stimulant). Its stimulatory effect is due to the presence of unmethylated CG dinucleotides in a particular base context designated CG-containing DNAs or CG oligonucleotides (ODNs).

Peptidoglycans are present in both Gram-positive and Gram-negative bacteria. Peptidoglycans are composed of long linear sugar chains of alternating N-acetyl glucosamine (GlcNac) and N-acetyl muramic acid (MurNac) that are interlinked by peptide bridges to form a large macromolecular structure. Peptidoglycans are recognised by NOD-like receptors, such as NOD1 or NOD2, and hence, peptidoglycans are NLR-stimulants.

Activation of TLRs or NLRs results in the translocation of the transcription factor, NF-κB, to the nucleus. NF-κB is a key transcription factor in the inflammatory cascade, and it initiates the transcription of pro-inflammatory cytokines to trigger an acute phase response. Examples of pro-inflammatory cytokines include interleukin (IL)-1, IL-6, IL-12, IL-15, IL-18 and/or TNF-α. Endothelial markers of inflammation are also induced by TLR-stimulation and may include the expression of adhesion molecules, such as inter-cellular adhesion molecule 1 (ICAM-1), vascular cell adhesion molecule-1 (VCAM-1) and E-selectin, and the chemokines such as IL-8 and monocyte chemoattractant protein (MCP)-1. Example 6, and FIGS. 14 and 15, shows that mice treated with LPS showed a ~3-fold increase in expression of intercellular adhesion molecule (ICAM-1) and a ~7-fold increase in expression of vascular cell adhesion molecule (VCAM-1). Both of these molecules are key mediators of inflammation in the vasculature and play a central role in the progression of atherosclerosis and other inflammatory diseases. These results therefore confirm that LPS delivered by the oral route can result in increases in inflammatory markers systemically.

TLR stimulation also promotes the accumulation of lipid in macrophages to promote a "foam-cell" phenotype, which may be of relevance to atherosclerosis.

The assay of the first aspect or the apparatus of the second aspect of the invention may be an in vitro system. The assay system may be a cell-based system comprising cells which express at least one TLR or at least one NLR. The cells of the assay system may be cells which do not normally express TLRs, such as HEK cells. The cells which do not normally express TLRs may be transfected with specific TLRs of interest. Preferably, the assay system expresses at least 2, 3, 4, 5, 6, 7, 8, 9, 10 TLRs and/or at least 1 or 2 NLRs. More preferably, the assay system expresses TLR-2, TLR-4 and/or TLR-5.

The assay system may further comprise proteins which enable efficient activation of TLRs or NLRs. These proteins may be myeloid differentiation-2 (MD2) and CD14 (cluster of differentiation-14). Lipopolysaccharide (LPS) induces inflammatory activation through the TLR4/MD-2/CD14 complex. The presence of these proteins may enhance the sensitivity of the assay system.

The concentration, value or amount of TLR-stimulant or NLR-stimulant may be determined in one embodiment of the assay or apparatus of the invention by measuring the amount of secretion of pro-inflammatory cytokines or chemokines secreted by the cells in the assay of the invention. Suitable pro-inflammatory cytokines may be IL-1, IL-6, IL-12, IL-15, IL-18 and/or TNF-α. Preferably, the pro-inflammatory cytokine is IL-6, IL-1 and/or TNF-α. A suitable chemokine may be IL-8 or MCP-1.

The TLR-stimulant or NLR-stimulant may be capable of increasing the secretion of cytokines and/or chemokines by at least 20%, 50%, 100%, 150%, 200%, 250% or at least 300% compared to the amount of cytokines and/or chemokines which are present in the absence or at the basal level of the TLR-stimulant in the assay system.

The cytokine or chemokine levels may be measured by standard assays known to the skilled technician. For example, a suitable assay is ELISA. ELISAs work by capturing specific antigens of interest (e.g. cytokines or chemokines) on an immobilised plastic surface (typically in a microtitre plate) using a cytokine specific antibody which has been preadsorbed to said plate. Bound cytokine in a sample is then detected using a second antibody specific for an alternative epitope on the same cytokine or chemokine of interest. The amount of bound secondary antibody is proportional to the amount of cytokine/chemokine in the sample, and is quantified by means of a peroxidase-based conjugate covalently attached to the antibody using a colorimetric reagent system. ELISAs are standardised relative to recombinant cytokines or chemokines of interest.

In another embodiment of the assay or apparatus of the invention, the concentration, value or amount of TLR-stimulant may be determined by measuring the amount NF-κB activity. NF-κB is a transcription factor. Therefore, NF-κB activity may be measured by a reporter system which is activated by NF-κB.

The TLR-stimulant or NLR-stimulant may be capable of increasing NF-κB activity by at least 20%, 50%, 100%, 150%, 200%, 250% or at least 300% compared to the amount of NF-κB activity which occurs in the absence or at the basal level of the TLR-stimulant or the NLR-stimulant in the assay system.

In one embodiment, the reporter system may be a bioluminescent system, which may for example be based upon the reaction of luciferase and luciferin. The reporter system may comprise a reporter gene which is under the control of a promoter that is sensitive to transcription factors activated by TLRs or NLRs. Preferably, the promoter is sensitive to the transcription factor, NF-κB.

The quantity of TLR-stimulants or NLR stimulants may be presented as a relative biological activity with respect to a known stimulant of TLR or NLR which elicits a dose-dependent immune response. The known stimulant of TLR may be LPS, BLP or flagellin. The BLP may be $Pam_3CSK_4$. The flagellin may be flagellin from S. typhimurium or any other motile bacterium. The known stimulant of NLR may comprise a bacterial peptidoglycan. As illustrated in Example 1, NF-κB activities at a series of LPS concentrations were measured. The quantity of TLR-stimulants present in each foodstuff was presented as a relative biological activity with respect to LPS.

An example of one embodiment of the assay or apparatus of the invention is illustrated in Example 1, in which the orally-ingestible sample is a foodstuff, and is described briefly below. HEK-293 cells, which do not normally express TLRs, may be transfected with specific TLRs of interest, and an NF-kB-dependent reporter construct. Transfected cells may be challenged with TLR-stimulant-containing samples and the relative biological activity of these TLR-stimulants measured by comparison of the extent of fold-induction of NF-kB reporter relative to a standard curve prepared from a range of concentrations of an established TLR2 or TLR4 stimulant, such as $Pam_3CSK_4$ or LPS. CD14 and MD2 constructs may additionally be transfected into the HEK-293 cells to enhance sensitivity of transfectants to low concentrations of TLR-stimulants in samples. NF-kB activation is measured by quantifying the amount of firefly luciferase in lysates prepared from challenged cells using luminometry.

An increased or elevated concentration of TLR-stimulant or NLR-stimulant (i.e. PAMP) in the sample of the test foodstuff may be indicative of the inflammation risk of that foodstuff. The concentration of TLR-stimulant or NLR stimulant (i.e. PAMP) may be compared to a reference for concentrations of TLR-stimulant or NLR-stimulant known to represent an inflammation risk. The reference value may be one which has previously been established through analytical studies. The value may correspond to the concentration of TLR-stimulant or NLR-stimulant capable of causing inflammation in a subject, regardless of their sex, age, body-mass index (BMI) or ethnic origin.

For example, for non-diabetic individuals in a population, the mean serum level of LPS may be about 0.1-0.8 μg/ml. Levels of circulating LPS above ~1 μg/ml may promote systemic inflammation in a dose-dependent manner. The inventor's mathematical models predict that 200 g of foodstuff containing >100 ng endotoxin per gramme of foodstuff may transiently increase circulating endotoxin levels above 1 μg/ml in human subjects.

Therefore, in one embodiment of the invention, the increased concentration of lipopolysaccharide (LPS) compared to the reference concentration, as determined by the assay of the first aspect or the apparatus of the second aspect, may be more than 50 ng/g foodstuff, preferably more than 100, 150, 200 or 250 ng/g foodstuff. The increased concentration of LPS may be in the range of 50 ng/g to 5 μg/g foodstuff, more preferably in the range of 100 ng/g to 1 μg/g foodstuff, or more preferably in the range of 150 ng/g to 500 ng/g foodstuff.

Therefore, in another embodiment of the invention, the increased concentration of bacterial lipopeptides compared to the reference concentration may be more than 150 ng/g foodstuff, preferably more than 200, 250, 300 or 350 ng/g foodstuff. The increased concentration of lipopeptides may be in the range of 150 ng/g to 15 μg/g foodstuff, more preferably in the range of 300 ng/g to 3 μg/g foodstuff, or more preferably in the range of 450 ng/g to 1.5 μg/g foodstuff. Assuming similar levels of absorption of lipopeptide, foodstuffs containing >300 ng lipopeptide-equivalents per gramme of food may promote inflammation in human subjects.

In a further embodiment of the invention, the increased concentration of flagellin compared to the reference concentration, as determined by the assay of the first aspect or the apparatus of the second aspect, may be more than 50 ng/g foodstuff, preferably more than 100, 150, 200 or 250 ng/g foodstuff. The increased concentration of flagellin may be in the range of 50 ng/g to 5 μg/g foodstuff, more preferably in the range of 100 ng/g to 1 μg/g foodstuff, or more preferably in the range of 150 ng/g to 500 ng/g foodstuff.

The increased concentration of peptidoglycan may be more than 50 ng/g foodstuff, preferably more than 100, 150, 200 or 250 ng/g foodstuff. The increased concentration of peptidoglycan may be in the range of 50 ng/g to 5 μg/g foodstuff, more preferably in the range of 100 ng/g to 1 µg/g foodstuff, or more preferably in the range of 150 ng/g to 500 ng/g foodstuff.

Figure 1:
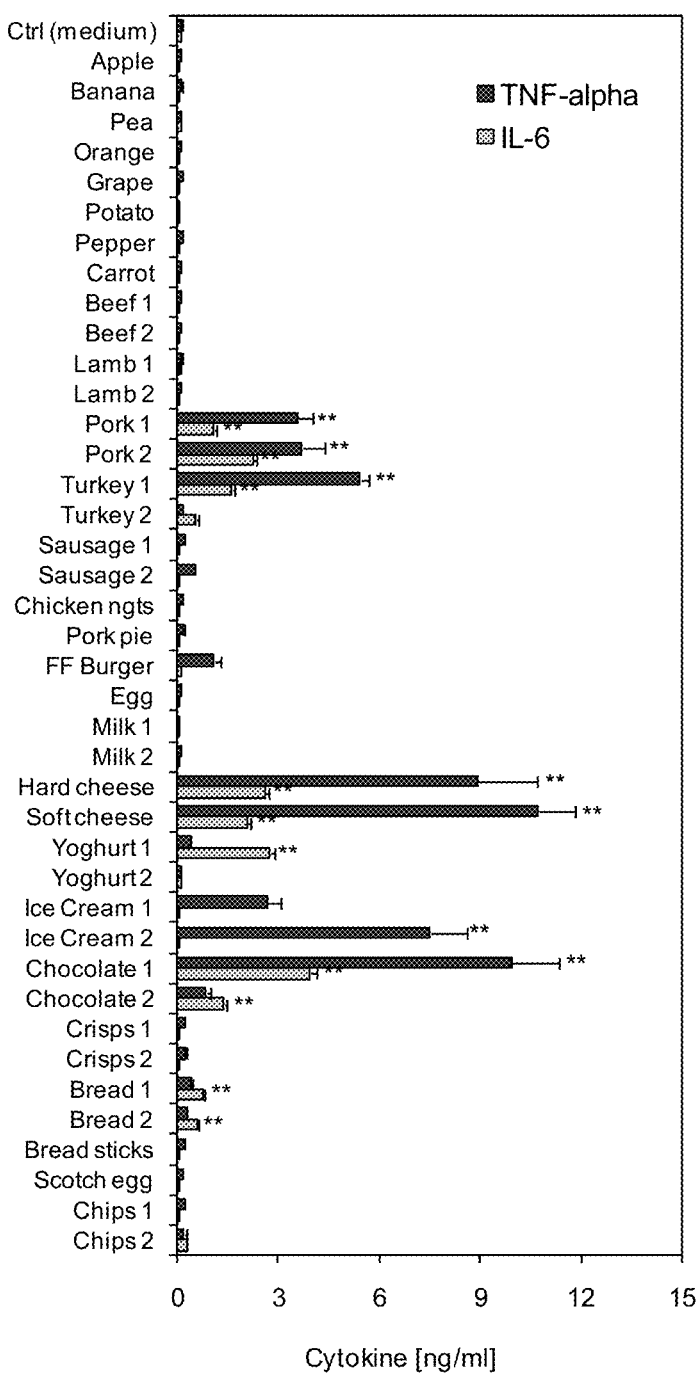
FIG. 1 illustrates the induction of monocyte cytokine secretion by sterile food extracts. Human primary monocytes were cultured with filter-sterilised food extracts diluted 1:20 in tissue culture medium. Secretion of TNF-α and IL-6 was measured at 4 h and 18 h respectively. The results are shown in a bar chart demonstrating the amount of cytokines measured. Results are mean±SEM of four experiments: monocytes from a different subject were used in each experiment. Black bars—TNF-α; grey bars—IL-6; Ngts—processed nuggets; FF—purchased from a 'fast food' outlet. **P<0.001 vs medium alone.
Figure 2:
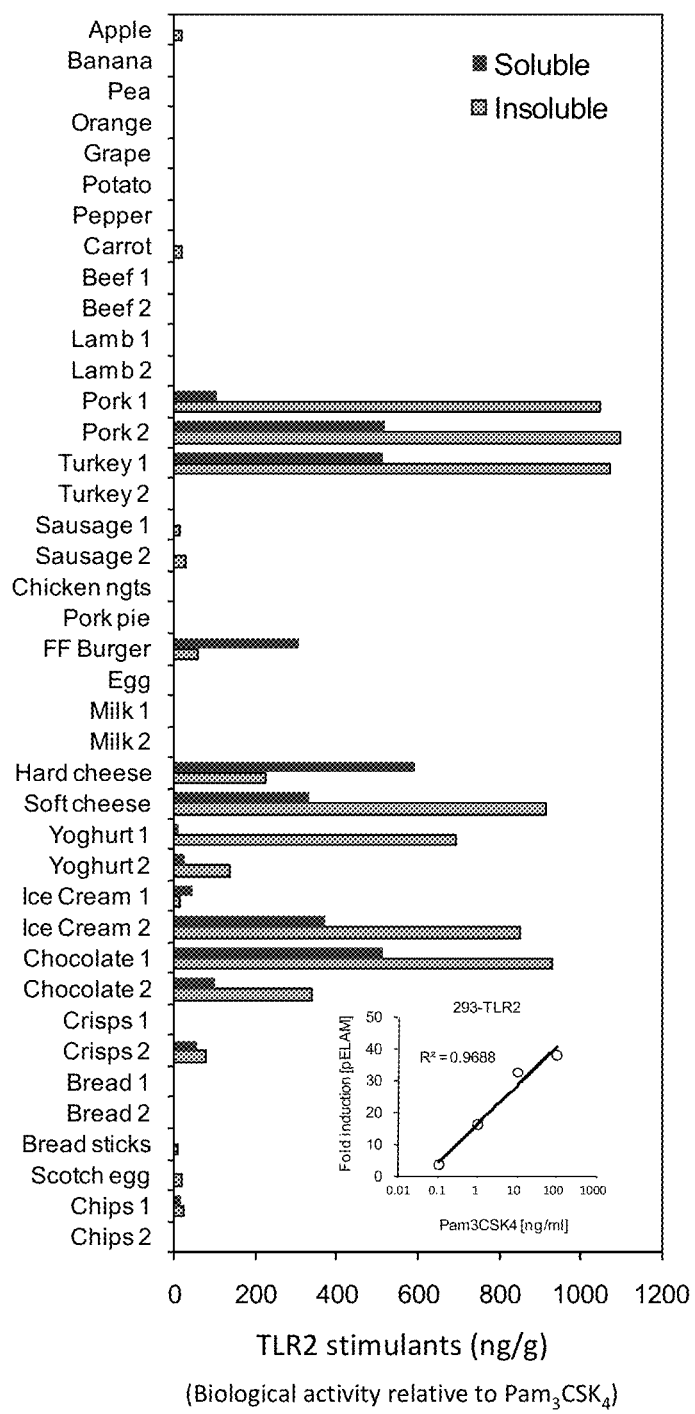
FIG. 2 shows quantification of TLR-2-stimulants in food extracts. Filter-sterilised food extracts (representing soluble food-borne TLR-stimulants) or heat-killed food suspensions (representing insoluble food-borne TLR-stimulants) were diluted 1:20 in tissue culture medium and applied to HEK-293 cells transfected with NF-κB reporter, CD14 and TLR-2. Reporter activity was measured at 18 h and converted to lipopeptide-equivalents using standard curves on the same plate using $Pam_3CSK_4$ as standard. The results are shown in a bar chart demonstrating the amount of TLR-2 stimulants (i.e. biological activity relative to $Pam_3CSK_4$) measured. A typical standard curve for measurement of biological activity relative to $Pam_3CSK_4$ is also shown (inset). Black bars—soluble food-borne TLR-stimulants; grey bars—insoluble food-borne TLR-stimulants.
Figure 3:
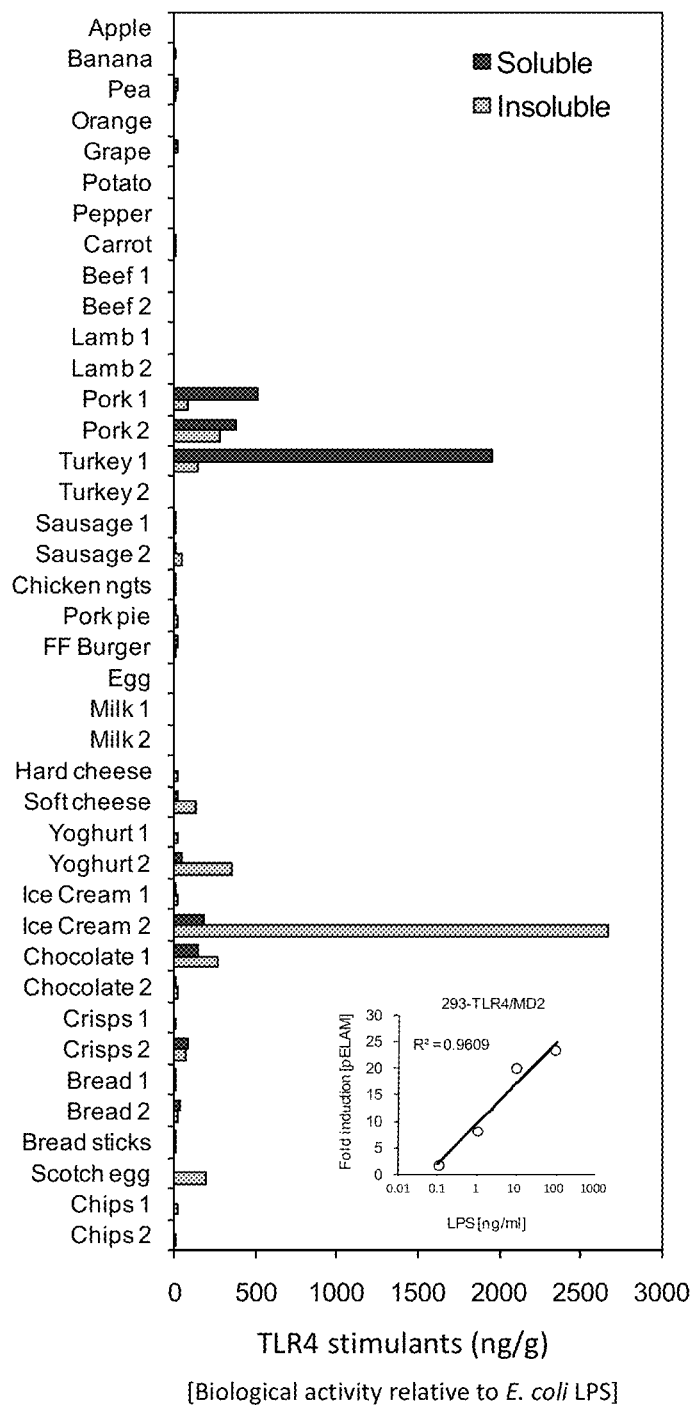
FIG. 3 shows quantification of TLR-4-stimulants in food extracts. Filter-sterilised food extracts (representing soluble food-borne TLR-stimulants), or heat-killed food suspensions (representing insoluble food-borne TLR-stimulants) were diluted 1:20 in tissue culture medium and applied to HEK-293 cells transfected with NF-κB reporter, CD14, TLR-4 and MD2. Reporter activity was measured at 18 h and converted to LPS-equivalents using standard curves on the same plate using *E. coli* R1 LPS as standard. The results are shown in a bar chart demonstrating the amount of TLR-4 stimulants (i.e. biological activity relative to LPS) measured. A typical standard curve for measurement of biological activity relative to LPS is also shown (inset). Black bars—soluble food-borne TLR-stimulants; grey bars—insoluble food-borne TLR-stimulants.

The foodstuff may be fresh, raw, cooked, pre-cooked or processed. The foodstuff may be bought in a container or as a consumable, such as from a fast-food outlet. The foodstuff may be a fruit, chocolate, ice-cream, meat, vegetable, bread or dairy product. Example 1 and FIGS. 1-3 provide examples of suitable foodstuffs, which may be tested. The inventor has found that PAMPs are resistant to low pH or protease treatment. The foodstuff may be extracted or dissolved.

An example of another embodiment of the assay or apparatus of the invention is illustrated in Example 5, in which the orally-ingestible sample is saliva. An increased or elevated concentration of TLR-stimulant or NLR-stimulant (i.e. PAMP) in the saliva sample may be indicative of the inflammation risk. The concentration of TLR-stimulant or NLR stimulant (i.e. PAMP) may be compared to a reference for concentrations of TLR-stimulant or NLR-stimulant known to represent an inflammation risk. The reference value may be one which has previously been established through analytical studies. The value may correspond to the concentration of TLR-stimulant or NLR-stimulant capable of causing inflammation in a subject, regardless of their sex, age, body-mass index (BMI) or ethnic origin.

For example, the median level of soluble TLR2 stimulants in saliva of healthy patients may be about 80 ng/ml, and the median level of soluble TLR4 stimulants in the saliva of healthy patients may be about 7 ng/ml. Thus, the reference value for a TLR2-stimulant may be about 80 ng/ml saliva, and for a TLR4 stimulant may be about 7 ng/ml saliva.

Figure 9:
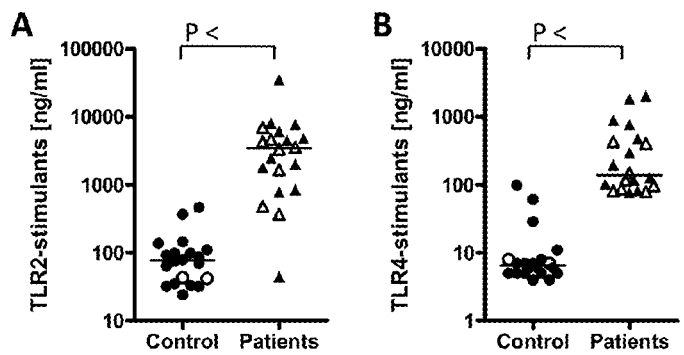
FIG. 9 shows the quantification of TLR-stimulants in filter-sterilised saliva. The biological activities of soluble stimulants of TLR2(A) and TLR4 (B) were quantified relative to $Pam_3CSK_4$ and *E. coli* LPS standards, using TLR-transfected HEK-293 cells as described in the materials and methods, in filter-sterilised saliva from healthy subjects (n=20) and periodontitis patients (n=20). Open symbols represent smokers.

The inventor has surprisingly found that soluble TLR2- and TLR4-stimulants were approximately 20- and 50-fold more abundant in the saliva of periodontitis patients, respectively, as shown in FIG. 9. Therefore, in one embodiment of the invention, the increased concentration of TLR2-stimulant compared to the reference concentration, as determined by the assay or apparatus of the invention may be at least 5-, 10-, 15- or 20-fold higher. For example, the increased concentration of TLR2-stimulant may be at least 400, 600, 800 or 1000 ng/ml saliva. For example, the increased concentration of TLR2-stimulant may be in the range of 500 ng/ml to 5000 ng/ml saliva, more preferably in the range of 1000 ng/ml to 3000 ng/ml saliva, or more preferably in the range of 1500 ng/ml to 2000 ng/ml saliva.

In another embodiment, the increased concentration of TLR4-stimulant compared to the reference concentration, as determined by the assay or apparatus of the invention may be at least 5-, 10-, 20-, 30-, 40- or 50-fold higher. For example, the increased concentration of TLR4-stimulant may be at least 35, 70, 100, 140, 300 or 350 ng/ml saliva. For example, the increased concentration of TLR4-stimulant may be in the range of 50 ng/ml to 2000 ng/ml saliva, more preferably in the range of 100 ng/ml to 1000 ng/ml saliva, or more preferably in the range of 200 ng/ml to 500 ng/ml saliva.

In a third aspect of the invention, there is provided the use of a Toll-like receptor (TLR) stimulant or a nucleotide-binding oligomerisation domain (NOD)-like receptor (NLR) stimulant as an inflammatory marker in an assay for determining the inflammation risk of an orally-ingestible biological sample.

For example, the orally-ingestible biological sample may be saliva or a foodstuff.

An inflammatory marker may be an agent that causes inflammation in the body of a subject under test. The inflammatory marker may be a stimulant or stimulants of TLR-1-9 and/or 10. The inflammatory marker may be a stimulant or stimulants of NOD1 and/or NOD2. Alternatively, the inflammatory marker may be a combination of TLR- and NLR-stimulants. Preferably, the inflammatory marker is a TLR-2, TLR-4 or TLR-5 stimulant.

Ingesting biological samples such as saliva or foodstuffs with high inflammation risk may increase the risk that an individual may suffer from a chronic inflammatory disease. These diseases include metabolic or cardiovascular conditions or diseases, such as periodontitis, non-alcoholic fatty liver disease (NAFLD), atherosclerosis, coronary artery disease, metabolic syndrome, hyperinsulinaemia, insulin resistance, type 2 diabetes mellitus (T2DM), arthritis, psoriasis, Crohn's disease or ulcerative colitis. Thus, these diseases may be avoided using the assay and apparatus of the invention to test foodstuffs or saliva.

Periodontitis is a chronic inflammatory disease of the gums, which begins with gingival bleeding and progresses to pocket formation, destruction of tooth-attachment ligaments and alveolar bone, and eventually loss of teeth. It is believed to be caused or accelerated in some way by excessive responsiveness to certain bacteria in the mouth, which may be of a different type in some people. The incidence of periodontitis is around 15% in the general population but up to 30% in some populations. The incidence of periodontitis increases with age, particularly above age 50.

As described in Example 5, the inventor has developed a robust bioassay for quantifying the relative biological activities of TLR-stimulants in human saliva using HEK-293 cells transfected with specific TLRs and NF-κB reporter. They have examined the profile of TLR2, TLR4 and TLR5 stimulants expressed by a panel of 13 major oral bacteria, and quantified the extent of shedding of such stimulants by a model enterobacterial organism to yield a first estimate of the relative contributions that may be made by oral and enteric bacteria to the PAMP content of the small intestine. As shown in FIG. 9, soluble lipopeptide and LPS levels are ~20-50 fold higher in saliva of patients with periodontitis compared to healthy subjects. The inventor believes that he is the first to demonstrate an increase in salivary PAMPs in subjects having periodontitis. This was totally unexpected since the total bacterial load in saliva of periodontitis patients is similar to that of healthy subjects (Mager et at J Clin Periodontol 2003, Mantilla Gómez et at J Clin Periodontol 2001). Furthermore, the assay of the invention has also revealed that about 20% of healthy subjects have raised levels of salivary endotoxin but do not yet have periodontitis, and this status is stable with time.

Accordingly, the assay of the invention can be advantageously used as a non-invasive way of identifying people at risk of developing periodontitis. This is particularly useful because people could be screened (for example by post), and then offered advice, either to visit a dentist if PAMPs levels are very high, or if levels are only moderately raised, to begin a specific dental hygeine programme, such as increased frequency of toothbrushing, use of bactericidal mouthwashes and/or flossing etc. in order to prevent progression to established disease. Because periodontitis is often relatively painless, many people do not visit a dentist to attend to problems early. The inventor believes therefore that periodontitis may be under-diagnosed, and so the assay of the invention can be used to increase early detection of the disease.

The assays and apparatuses of the invention may also be used to predict the risk of developing diabetes or cardiovascular disease. There is literature which shows strong correlations between periodontitis and cardiovascular disease (e.g. Beck et al, Arterioscler Thromb Vasc Biol, 2001, 21:1816-1822; Tonetti, J Clin Periodontol, 2009, 36 Suppl 10:15-19)

and diabetes (e.g. Teeuw et al, Diabetes Care, 2010, 33:421-427). Thus, identifying subjects at risk of periodontitis also identifies them as being at risk of cardiovascular disease and insulin resistance. Although not wishing to be bound by hypothesis, the inventor believes that periodontitis patients are at a higher risk of developing cardiovascular disease and insulin resistance (and therefore diabetes) because injection of lipopeptide or LPS dramatically accelerates atherosclerosis and insulin resistance in mice. Elevated levels of LPS in plasma measured by LAL assay are also present in human subjects with atherosclerosis or insulin resistance relative to healthy subjects. To date, no studies have ever looked at oral LPS or lipopeptide in such subjects.

Studies have shown that diabetic or obese individuals and animal models may be more sensitive to the effects of LPS. Therefore, there is a need to monitor an individual's diet in an attempt to prevent these chronic inflammatory diseases.

Accordingly, in a fourth aspect of the invention, there is provided a method of monitoring a subject's diet for inflammation risk, the method comprising analysing the concentration of a Toll-like receptor (TLR) stimulant or a nucleotide-binding oligomerisation domain (NOD)-like receptor (NLR) stimulant in at least one test foodstuff of a subject's meal, comparing this concentration with a reference concentration of TLR-stimulant or NLR-stimulant known to represent an inflammation risk, wherein an increased concentration of TLR-stimulant or NLR-stimulant in the test foodstuff indicates that the foodstuff, and thus diet, causes inflammation.

When assessing the inflammatory risk of a foodstuff for a subject, the level of TLR-stimulant or NLR-stimulant or PAMP in the food sample may be combined with other data taken from the subject. Such data may include one or more of gender, age, fat mass, body mass index (BMI) and/or ethnicity. The quantitative relationships between such additional patient parameters and the relative risk of developing the various inflammatory diseases will be familiar to one skilled in the art.

The subject may be healthy. However, the subject may be or is susceptible to chronic inflammatory diseases. The individual may also be susceptible to metabolic or cardiovascular conditions or diseases, such as obesity, non-alcoholic fatty liver disease (NAFLD), atherosclerosis, coronary artery disease, metabolic syndrome, hyperinsulinaemia, insulin resistance, type 2 diabetes mellitus (T2DM), arthritis, psoriasis, Crohn's disease, ulcerative colitis or periodontitis. The individual may be diabetic or obese.

Clearly, once a subject's diet for inflammation risk has been monitored, it would be advantageous to be able to treat an individual to prevent them from developing inflammation, and any of the diseases mentioned above.

In a fifth aspect of the invention, there is provided a method of preventing a subject from developing inflammation, the method comprising:
 (i) determining the concentration of a Toll-like receptor (TLR) stimulant or a nucleotide-binding oligomerisation domain (NOD)-like receptor (NLR) stimulant in at least one foodstuff of a subject's meal;
 (ii) comparing this concentration with a reference concentration of a TLR-stimulant or NLR-stimulant known to represent an inflammation risk, wherein an increased concentration of TLR-stimulant or NLR-stimulant in the sample from the test foodstuff indicates that the foodstuff causes inflammation; and
 (iii) administering an anti-inflammatory agent to the subject when the concentration of TLR-stimulant or NLR-stimulant determined in step (i) is higher than the reference concentration.

The anti-inflammatory agent may be a non-steroidal anti-inflammatory drug (NSAID). The NSAID may be aspirin, ibuprofen (Advil or Motrin), naproxen sodium (Aleve), ketoprofen (Orudis KT), or acetaminophen (Tylenol or Panadol).

Alternatively, the anti-inflammatory agent may be an anti-LPS antibody, anti-TLR antibody or anti-NLR antibody. The anti-inflammatory agent may also be a TLR antagonist or NLR antagonist.

The inventor believes that it may also be advantageous to be able to determine which TLR-stimulants or NLR-stimulants may be present in a certain foodstuff, and in what quantity. Identification of the type of stimulant present in foodstuffs responsible for promoting inflammation may provide useful information that may be used to enable the identification and removal the source of the contaminant from the food preparation process, or specific therapeutics to neutralise the biological effects of the particular stimulant in vivo.

Thus, according to the sixth aspect of the invention, there is provided a method for determining, in a foodstuff, the identity of a PAMP which causes inflammation, the method comprising:
 (i) determining the concentration of a PAMP in a sample from a test foodstuff;
 (ii) comparing this concentration with a reference concentration of the PAMP known to represent an inflammation risk, wherein an increased concentration of PAMP in the sample from the test foodstuff compared to the reference concentration indicates that the foodstuff causes inflammation; and
 (iii) determining which Toll-like receptor (TLR) TLR and/or TLR-signalling pathway or nucleotide-binding oligomerisation domain (NOD)-like receptor (NLR) and/or NLR-signalling pathway has been activated when the concentration of PAMP determined in step (i) is higher than the reference concentration, wherein the activated TLR and/or TLR-signalling pathway or NLR and/or NLR-signalling pathway indicates the identity of the PAMP.

The determination step (iii) may be carried out in an assay system where only one TLR or NLR family member is expressed. Alternatively, the determination step (iii) may be carried out in an assay system where more than one TLR or NLR family members are expressed. Other methods that are familiar to the skilled technician for determining the identity of a compound may include mass-spectrometry or NMR.

In a further aspect, there is provided a method of reducing or pre-empting the risk of inflammation caused by a foodstuff at risk of being contaminated by a pathogen-associated molecular pattern (PAMP) or a microbe-associated molecular pattern (MAMP), the method comprising adding a Toll-like receptor (TLR)-signalling inhibitor to the foodstuff.

In another aspect, there is provided use of a Toll-like receptor (TLR)-signalling inhibitor for reducing or pre-empting the risk of inflammation caused by a foodstuff at risk of being contaminated by a pathogen-associated molecular pattern (PAMP) or a microbe-associated molecular pattern (MAMP).

Compounds that specifically inhibit signalling of one or more of the TLR family member(s) may be used to eliminate the TLR and/or TLR-signalling pathway, thereby identifying the pathway which the TLR-stimulant activates. Such compounds may be used as TLR-signalling inhibitors. For example, oxidised palmitoyl-arachidonyl phosphocholine (OxPAPC) specifically inhibits signalling via TLR-2 and TLR-4 signalling, but not other TLRs or cytokine receptors. Compounds that specifically inhibit signalling of one or more of the TLR-stimulant bioactivity may be also used to eliminate the TLR-signalling pathway, thereby identifying the pathway which the TLR-stimulant activates. Polymyxin-B (PMB) is a specific inhibitor of LPS-bioactivity.

Alternatively, compounds that specifically inhibit signalling of one or more of the NLR family member(s) or one or more NLR-stimulant bioactivity may be used to eliminate the NLR and/or NLR-signalling pathway, thereby identifying the pathway which the TLR-stimulant activates. The skilled person will appreciate that siRNA may be used to abolish NLR expression.

All of the features described herein (including any accompanying claims, abstract and drawings), and/or all of the steps of any method or process so disclosed, may be combined with any of the above aspects in any combination, except combinations where at least some of such features and/or steps are mutually exclusive.

EXAMPLES

Example 1

The inventor attempted to determine whether common foodstuffs may contain appreciable quantities of endotoxin, or other similar agents that may be capable of eliciting innate immune activation of human monocytes. In particular, the inventor chose to quantify the levels of stimulants of Toll-like receptor (TLR)-2, TLR-4 and TLR-5 in food extracts, as these receptors have been shown to play key roles in murine models of atherosclerosis and insulin resistance. Moreover, experimental administration of the ligands of TLR-2 and TLR-4, namely bacterial lipopeptides (BLP) and lipopolysaccharides (LPS), to animal models of these diseases has been shown to result in a marked increase in both atherosclerosis and insulin resistance.

Extracts were therefore prepared from 40 foodstuffs common to the Western diet, and the capacity of each to induce secretion of IL-6 and TNF-α from human monocytes was measured and compared with the abundance of stimulants of TLR-2, TLR-4 or TLR-5 in each foodstuff, as quantified using a TLR-transfectant based bioassay (Erridge et al., 2010, PLoS ONE, 5, 2, e9125). The inventor, furthermore, aimed to establish whether the biological activities of such stimulants may be sensitive to commonly used cooking regimes, or to low pH and protease environments similar to those that may be encountered in the stomach before entry to the small intestine, and whether they may reflect endogenous TLR-stimulants or microbial food-contaminants.

Materials and Methods
Preparation of Food Extracts

Fresh foods from four major categories (fruit and vegetables, dairy, meat and processed foods) were purchased from local supermarkets or retail food outlets and taken directly to the laboratory for same-day processing. All foods showed no obvious signs of spoilage or degradation and were well within advertised 'use-by' dates. Fruit and vegetables were peeled and chopped before processing in the uncooked form. Minced meats were also assayed in its uncooked form. Pre-cooked processed foods (including those purchased from fast-food outlets) were assayed in the cooked form as they would be bought or consumed. In each case, 25 g of fresh produce was homogenised in 250 ml phosphate buffered saline (PBS) using a domestic blender (full power for 1 minute) which was thoroughly cleaned and rinsed between samples. A 1 ml aliquot of each homogenate was then heat-sterilised (100° C. for 10 min) to represent the insoluble pathogen-associated molecular patterns (PAMPs), such as LPS and lipopeptide, present in each foodstuff (termed heat-killed food extract, HKF). A second aliquot of each food suspension was then clarified by centrifugation (13,000 g for 5 min) and the resulting supernatant was filter-sterilised (0.22 µm, Acrodisc) to represent the soluble PAMPs present in each sample (termed sterile-filtered food extract, StF). StF and HKF samples were stored at −20° C. before being assayed in a batch for BLP, flagellin and LPS content.

Challenge of Human Monocytes

Venous blood was collected by venepuncture from consenting healthy human subjects according to the guidelines laid down in the Declaration of Helsinki and all procedures involving human subjects were approved by the University of Leicester College of Medicine Research Ethics Committee. Written informed consent was obtained from all subjects. Peripheral blood mononuclear cells (PBMC) were prepared by density gradient centrifugation at 800 g for 25 min using Histopaque-1077 (Sigma). Recovered cells were washed twice in PBS solution, resuspended in RPMI/10% fetal calf serum (FCS) (Sigma) and plated in 96-well plates at $4 \times 10^5$ cells per well. Monocytes were prepared from PBMC by plastic adherence (1 h at 37° C.), followed by gentle washing to remove non-adherent cells. Remaining monocytes were then challenged by adding a 1:20 dilution of each sterile-filtered food extract in tissue culture medium. After incubation at 37° C. for 4 h, supernatants were removed for assay of TNF-α content by L929-cell bioassay as described in Delahooke et al. (1995, Infect. Immun. 63, 840-846), or IL-6 levels were measured by ELISA (R&D) after 18 h.

TLR-Transfection Reporter Assays and Quantification of TLR-Stimulants

For transfection assays, human embryonic kidney (HEK)-293 cells were plated in 96 well plates at $10^4$ cells per well and transfected after 24 h using Genejuice (Novagen) according to manufacturer's instructions. The following amounts of constructs were added to each well: 30 ng of human TLR-2, TLR-5 or TLR-4 (co-expressing MD-2), 30 ng of pCD14 and 10 ng of NF-κB-sensitive luciferase-reporter construct (pELAM). Cells were grown for 3 days post transfection prior to 18 h challenge. Promoter expression was calculated as fold induction relative to cells cultured in medium alone +/−SD. Endogenous expression of TLRs in HEK-293 has been ruled out by RT-PCR by the inventor.

*E. coli* R1 (NCTC 13114) lipopolysaccharides (LPS) was prepared as described previously and was repurified by phenol/water extraction to remove TLR-2-stimulating lipopeptide contaminants (Delahooke et al., 1995). Synthetic bacterial lipopeptide $Pam_3CSK_4$ and *S. typhimurium* flagellin were purchased from Invivogen. *S. typhimurium* flagellin, LPS or $Pam_3CSK_4$ were unable to activate HEK-293 cells transfected with CD14 alone, or with non-corresponding TLRs (data not shown).

Standard curves of bacterial lipopeptides (BLP), LPS and flagellin were prepared using 10-fold dilutions from 100 ng/ml to 0.1 ng/ml in duplicate. Log-transformed PAMP concentrations were then plotted against fold-induction of NF-κB reporter to generate a standard curve. This was used to estimate concentrations of TLR-2- and TLR-4-stimulants present in each food sample relative to standard $Pam_3CSK_4$, LPS or flagellin as described previously (Erridge et al., 2010). The quantity of TLR-stimulants present in each extract is therefore presented as a relative biological activity with respect to $Pam_3CSK_4$, LPS or flagellin. For example, results presented as 200 ng/g BLP-equivalent means that each gramme of food contains TLR-2-stimulants with a capacity to stimulate TLR-2-signalling equal to that of 200 ng $Pam_3CSK_4$. Food extracts were measured at 1:10 dilution in DMEM/10% FCS in duplicate. If signals exceeded the range of the standard curve, further dilutions were prepared and reassayed. As transfected cells were sensitive to a minimum of 0.1 ng/ml LPS or $Pam_3CSK_4$, the minimum concentration of food-borne PAMPs detectable by the assay was 10 ng PAMP per gramme food.

PAMP Treatments

To determine whether the biological activities of LPS or lipopeptide may be inhibited by typical cooking times and temperatures, solutions of E. coli LPS or $Pam_3CSK_4$ (100 ng/ml) were prepared in normal saline. Samples were then maintained at 100° C. for 1-120 min, before cooling, diluting 1:10 in DMEM/10% FCS and applying to HEK-293 cells transfected with TLR-2 or TLR-4/MD2 for measurement of capacity to induce TLR-signalling as described above. Alternatively, LPS and $Pam_3CSK_4$ aliquots were adjusted to pH 1.0 for 2 h or 3 h by addition of HCl. Samples were then neutralised by addition of NaOH solution and applied to TLR-transfected HEK-293 cells as described above.

As a negative control, parallel samples were supplemented with an equal molarity of NaCl to account for increased salinity of samples due to acid/base neutralisation. In separate experiments, LPS or lipopeptide preparations were treated with proteinase-K at 37° C. for 1 h, then heated at 80° C. for 10 minutes to inactivate enzyme prior to addition to transfected HEK-293 cells. Control samples were also heat-treated for 10 minutes.

In some experiments, 10 µg/ml polymyxin-B was added to samples for 10 minutes prior to assay to determine if TLR-4-stimulants were of LPS origin. In other experiments, monocytes were pretreated with 25 µg/ml oxidised palmitoyl-arachidonyl phosphocholine (OxPAPC) prepared by dry film air oxidation as described previously (Erridge et al., 2008, J. Biol. Chem., 283, 24748-24759) before addition of 100 ng/ml $Pam_3CSK_4$, LPS or food extracts.

Statistics

Results were compared by ANOVA using Tukey's or Dunnet's post-test. Differences were considered to be significant at $P<0.05$.

Results

Stimulation of Human Monocytes by Soluble Extracts of Common Foodstuffs

The soluble extracts of 40 commonly available foodstuffs were prepared by filter-sterilising a homogenate of each foodstuff to exclude intact bacterial cells. Each food product was processed on the same day as purchase, showed no signs of spoilage and was within the advertised 'use-by' date. A 1:20 dilution of each sterile filtered extract was then prepared in tissue culture medium and applied to human monocytes for 4 h. Although extracts of most foods did not stimulate TNF-α secretion, extracts of 3 minced meats, 2 cheeses, 1 ice cream and 1 chocolate product induced significant secretion of TNF-α relative to cells cultured in medium alone ($P<0.001$, FIG. 1). Very similar results were obtained using the monocytes of 4 different subjects, and also by measurement of monocyte secretion of IL-6 (FIG. 1).

The inventor's recent experiments have shown that this variability between similar products can be explained by the microbial burden in each food product at some point in its (pre-cooking) preparation. This depends on factors such as the temperature and time each product has been held at that temperature before assay, and the sterility of the processing environment.

Quantification of Stimulants of TLR-2, TLR-4 and TLR5 in Food Extracts

In order to investigate what factors may be responsible for the ability of some food extracts to promote cytokine secretion by monocytes, while related foods did not, the inventor next quantified the abundance of stimulants of TLR-2 and TLR-4 in both the soluble (StF) and insoluble (HKF) fractions of each food extract. These fractions were examined separately as it was considered that PAMPs that remain attached to bacteria are unlikely to translocate from the small intestine into the blood. Specifically, it has been shown that while intact bacteria are efficiently excluded from the circulation by intestinal epithelial cell tight junctions, a small fraction of labelled soluble molecules, particularly those with molecular weights<60 kDa, can translocate from the lumen of the small intestine into the circulation via non-specific uptake mechanisms during the absorptive phase, remaining antigenically intact or biologically active after transport.

In terms of TLR-2-stimulants, it was found that most foods did not contain either detectable soluble or insoluble stimulants of TLR-2 (FIG. 2). However, 3 of the minced meats (two pork and one turkey), 1 cooked fast-food outlet burger, 2 cheeses, 2 ice creams and 2 chocolate products all contained detectable TLR-2-stimulants, with levels ranging from 55 to 588 ng/g in the soluble fraction, and 80 to 1,096 ng/g in the insoluble fraction, as measured in terms of their biological activities relative to the synthetic bacterial lipopeptide $Pam_3CSK_4$.

Next, because the limulus-amoebocyte-lysate (LAL) assay is readily confounded by common food constituents such as β-glucans, and generates a false-positive reaction to TLR-4 antagonist type LPS, the inventor found that it could not be used to detect TLR-4 stimulants in this type of study. To circumvent these problems, expression of the native human receptor for hexa-acyl LPS, TLR-4/MD2, was instead used to detect TLR-4-stimulants in each of the food samples. Examination of the abundance of TLR-4-stimulants using this technique revealed that most food extracts examined contained little or no detectable TLR-4 agonist-type molecules (FIG. 3). However, the same three minced meats which contained TLR-2 stimulants also contained abundant TLR-4-stimulants, while one ice cream, one yoghurt and one chocolate product also contained elevated endotoxin concentrations. Levels of TLR-4 stimulants in these products ranged from 50 to 1,959 ng/g in the soluble fraction, and 89 to 2,667 ng/g in the insoluble fractions, relative to E. coli LPS.

Measurement of TLR5 stimulants in each soluble extract using similar assays revealed that only 3 samples contained flagellin levels above 200 ng/g. Specifically, one yoghurt, one ice cream and one chocolate product contained soluble flagellin levels ranging from 240 to 376 ng/g, in terms of comparison to S. typhimurium flagellin standard. Notably, none of the food extracts induced NF-κB activation in HEK-293 cells transfected with CD14 and reporter alone, i.e. without TLR-2 or TLR-4 transfection, indicating that the food extracts did not possess inherent capacity to stimulate NF-κB signalling in these cells in the absence of TLR-2 or TLR-4 (data not shown).

To assess the reproducibility of these findings, three food extracts which were originally found to contain both TLR-2- and TLR-4-stimulants were subjected to repeat assays on three further occasions. These subsequent assays revealed very similar patterns of TLR-stimulants in each foodstuff, with inter-assay coefficient of variance CV for concentrations TLR-2-stimulants of ~27% and TLR-4-stimulant concentration of ~20% over 3 freeze-thaw cycles. This level of variation is typical for cell-based bioassays in which the useful dynamic range of the assay is spread over several orders of magnitude (i.e. from 10 ng/g to 10,000 ng/g in this case). Food extracts which were negative for TLR-stimulants in the first screen were also negative in subsequent assays, indicating that the results are not due to spontaneous contamination arising during sample processing or measurement (data not shown).

Capacity of Food Extracts to Stimulate TNF-α Secretion is Dependent on TLR-2 and TLR-4

Figure 4:
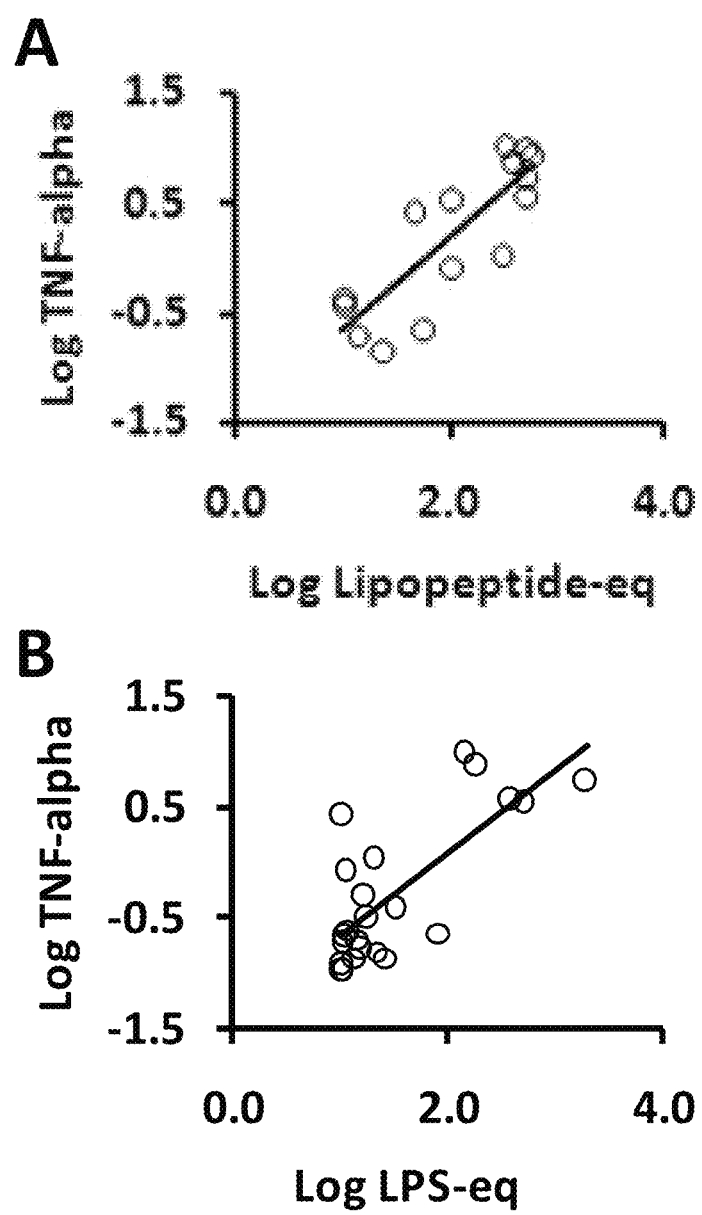
FIG. 4 illustrates the positive correlation between food PAMP content and induction of TNF-α. (A) Monocyte TNFα secretion were correlated with the content of bacterial lipopeptides (TLR-2 stimulants); r=0.837. (B) Monocyte TNFα secretion were correlated with the content of lipopolysaccharide (LPS) (TLR-4 stimulants) r=0.745.
Figure 5:
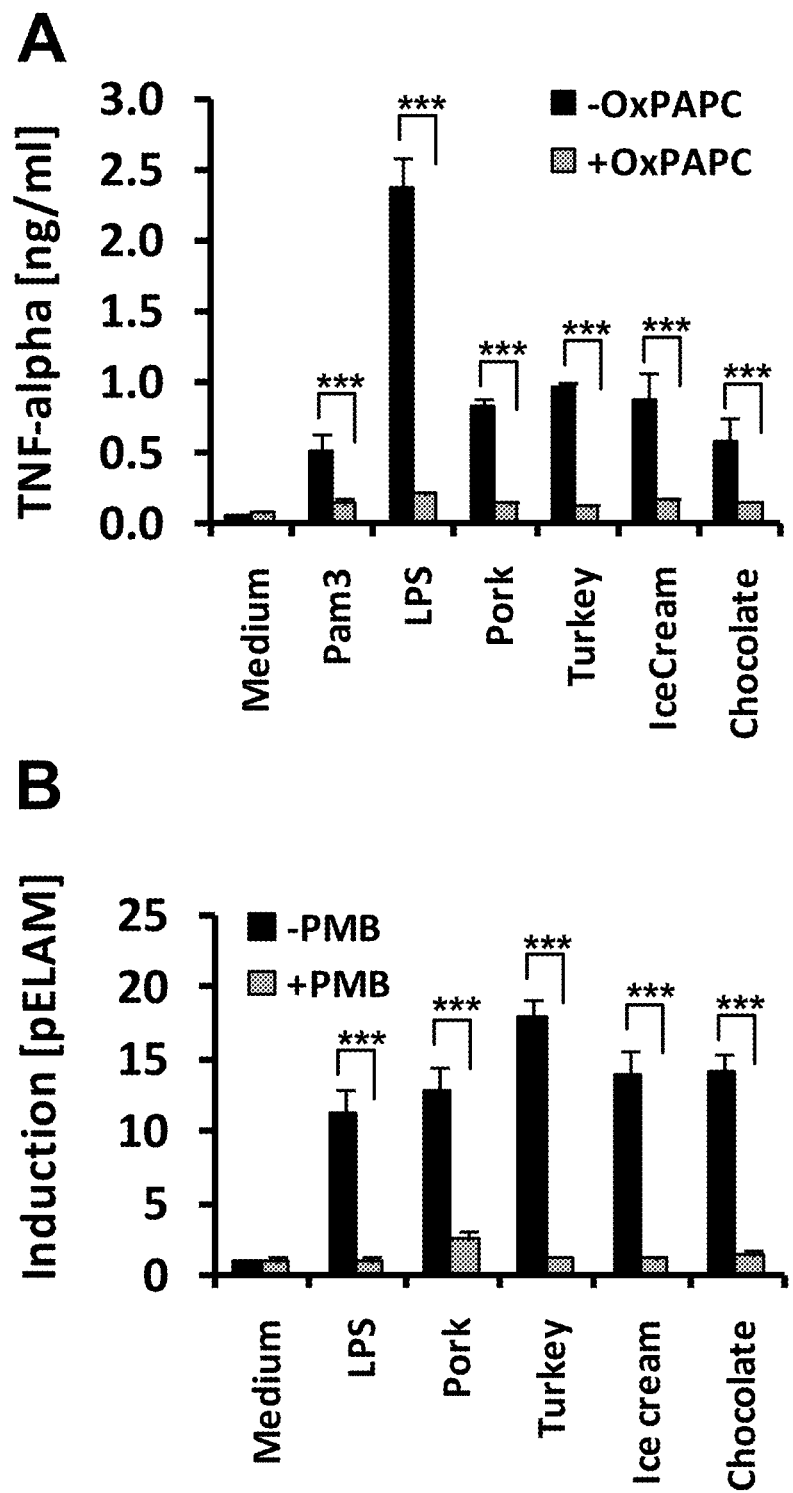
FIG. 5 shows the effect of inhibition of TLR-2 and TLR-4 on food extract-induced inflammatory signalling. (A) Primary human monocytes were incubated with filter-sterilised food extracts previously established to contain LPS and BLP in the presence or absence of 25 µg/ml OxPAPC, a specific inhibitor of signalling via TLR-2 and TLR-4, but not other TLRs. TNF-α secretion was measured at 4 h. Black bars—in the absence of OxPAPC; grey bars—in the presence of OxPAPC. (B) Capacity of LPS-containing food extracts to stimulate TLR-4 signalling in transfected HEK-293 cells was measured in the presence or absence of polymyxin-B (PMB), a specific inhibitor of LPS-bioactivity. Results are mean±SD of triplicate measurements made in one experiment representative of at least 3 separate experiments. Black bars—in the absence of PMB; grey bars—in the presence of PMB. *** P<0.001.

Monocyte TNF-α secretion was found to correlate more closely with content of TLR-2-stimulants ($r=0.837$, $P<0.0001$) than with content of TLR-4-stimulants ($r=0.745$, $P<0.0001$), when food products with detectable PAMP levels were compared (FIG. 4). IL-6 levels were less well correlated with TLR-2- and TLR-4-stimulants ($r=0.403$, and $r=0.594$, respectively). No significant correlation was observed between cytosine expression and endotoxin as measured by the kinetic lumulus (LAL) method, and LAL measurements also did not correlate significantly with TLR2 or TLR4 stimulants measured by TLR-bioassay, thereby adding further confirmation to the lack of utility of the LAL assay to predict inflammatory risk. To determine if TLR-2- and TLR-4-stimulants are required for the induction of TNF-α secretion, human monocytes were treated with each foodstuff in the presence or absence of OxPAPC, a compound that has been shown to specifically inhibit signalling via TLR-2 and TLR-4, but not other TLRs or cytokine receptors. Combined blockade of TLR-2 and TLR-4 with OxPAPC completely abrogated TNF-α secretion in response to each stimulant-containing foodstuff (FIG. 5A).

Next, as it has been suggested that alternative ligands beyond LPS may also be capable of stimulating TLR-4-dependent signalling (such as saturated fatty acids and heat-shock proteins), the inventor examined the capacity of polymyxin-B to inhibit the TLR-4-stimulation induced by sterile-filtered extracts. Polymyxin-B is a cationic antibiotic that specifically binds LPS and sequesters it from the receptors of the innate immune system. Referring to FIG. 5B, the results show that polymyxin-B blocked TLR-4-signalling from each of the products examined, suggesting that the TLR-4-stimulants in the foodstuffs examined are endotoxins (i.e. LPS) and not other types of molecule.

Heat Stability of Lipopeptide, LPS and Flagellin

Figure 6:
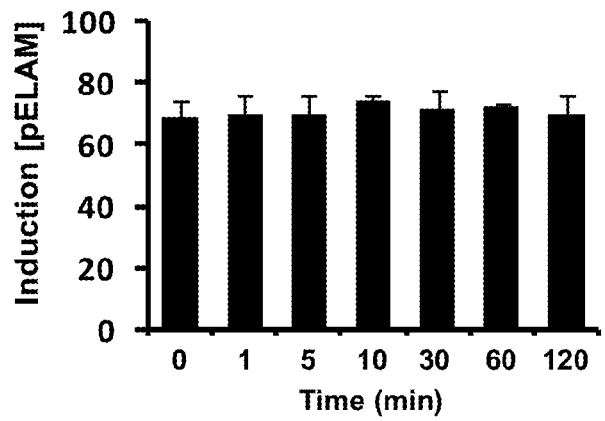
FIG. 6 illustrates the thermal stability of lipopeptide, LPS and flagellin. 100 ng/ml $Pam_3CSK_4$, *E. coli* LPS or flagellin in PBS was heated at 100° C. for 0-120 min. Samples were then cooled, diluted 1:10 in medium and induction of NF-κB-sensitive reporter (pELAM) was measured in HEK-293 cells transfected with TLR-2 (A), TLR-4/MD2 (B), or TLR5 (C). P<0.01 vs untreated PAMP. Results are mean±SD of triplicate measurements made in one experiment representative of at least 3 separate experiments. P<0.01.
Figure 6:
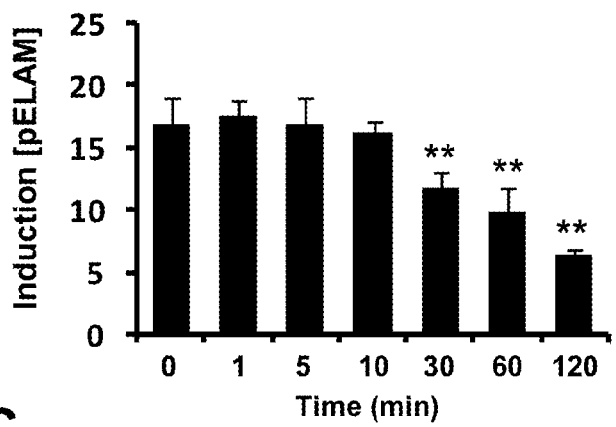
Figure 6:
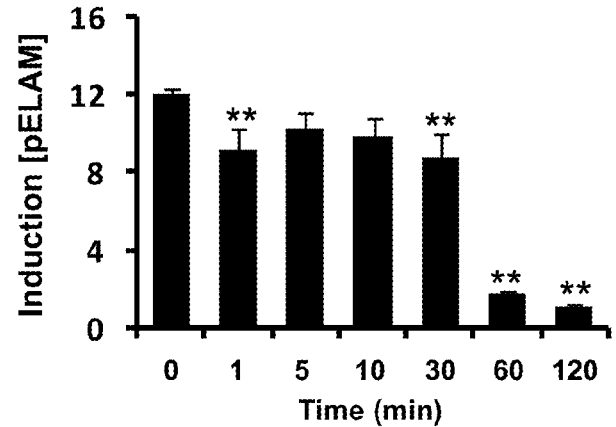

To determine whether food-borne lipopeptides, LPSs or flagellins may be destroyed by typical cooking temperatures or times, aliquots of $Pam_3CSK_4$, *E. coli* LPS and flagellin boiled in saline at 100° C. for up to 2 hours were tested for their remaining capacity to stimulate signalling via their respective TLRs. The biological activity of $Pam_3CSK_4$ was not measurably reduced by heating for up to 2 hours (FIG. 6A). LPS retained its biological activity up to around 10 minutes, but further heating led to a modest but significant reduction in biological activity after 30 minutes (FIG. 6B). By contrast, the biological activity of flagellin was almost completely abolished by 1 h (FIG. 6C). These results suggest that typical cooking times and temperatures are not likely to greatly reduce the biological activity of contaminating lipopolysaccharides or lipopeptides in food products.

Resistance of Lipopeptide, LPS and Flagellin to Low pH and Protease Treatment

Figure 7:
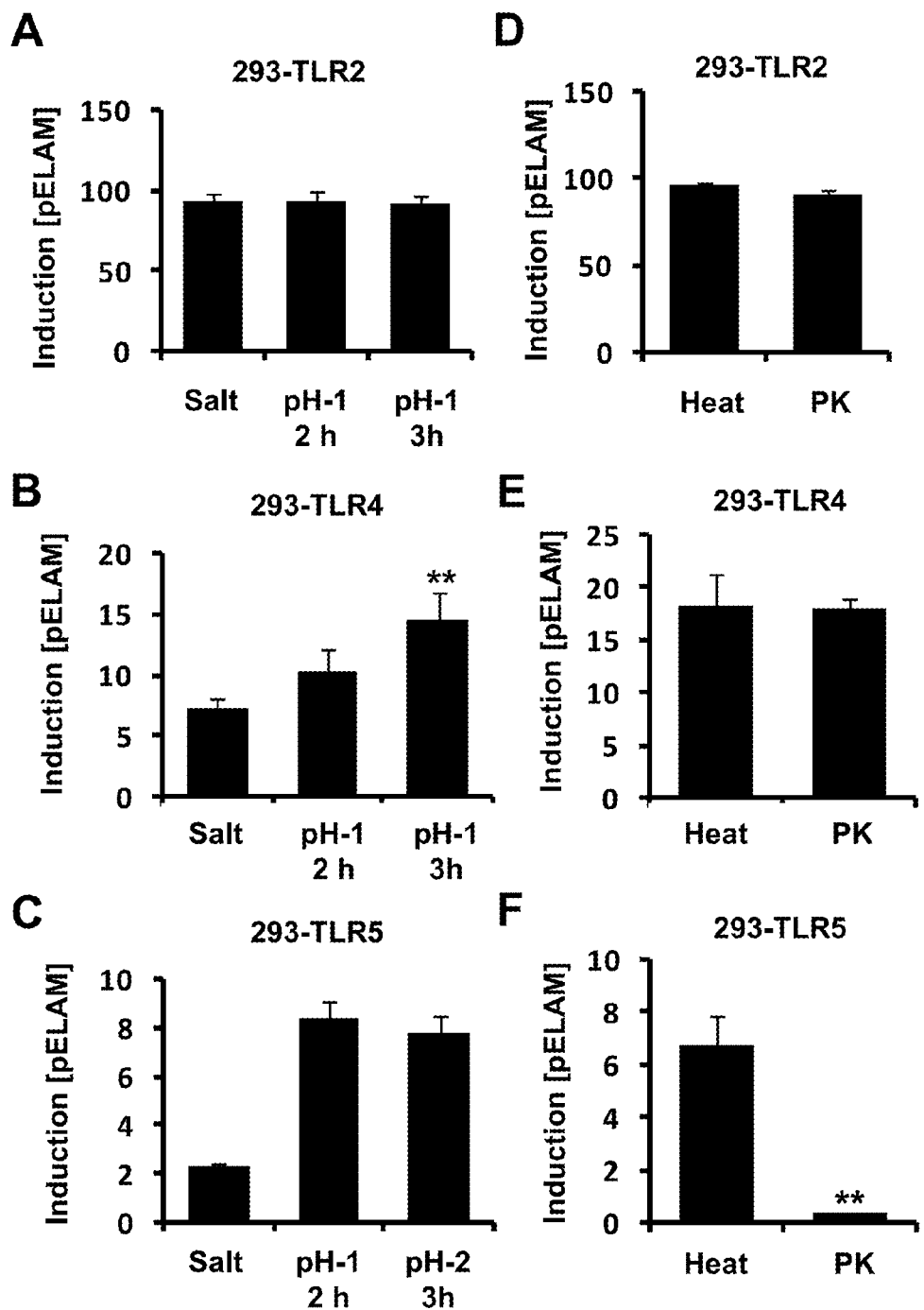
FIG. 7 shows the effects of low pH and protease treatment on biological activities of lipopeptide, LPS and flagellin. 100 ng/ml of each of $Pam_3CSK_4$ (A and D), *E. coli* LPS (B and E) or flagellin (C and F) was adjusted to pH 1.0 with HCl for 2 h or 3 h, then neutralised with NaOH, or treated with equivalent molarity NaCl at 37° C. Capacity of each PAMP to signal their corresponding TLR, i.e. $Pam_3CSK_4$ via TLR-2 (A), *E. coli* LPS via TLR-4 (B) or flagellin via TLR5 (C), was then measured in TLR-transfected HEK-293 cells. Alternatively, PAMPs were treated with proteinase-K at 37° C. for 1 h before heat-treatment at 80° C. for 10 minutes to neutralise enzyme (D-F). Results are mean±SD of triplicate measurements made in one experiment representative of at least 3 separate experiments. **P<0.01 vs untreated PAMP.

As ingested PAMPs must pass through the stomach before entry to the small intestine, the inventor next tested whether lipopeptide, LPS or flagellin may be resistant to low pH or protease treatment. Low pH (followed by neutralisation) did not affect the capacity of BLP to stimulate TLR-2, while the activity of LPS was markedly increased by low pH treatment, presumably due to release of lipid-A. Likewise, low pH increased the biological activity of flagellin, likely due to increased monomerisation, as expected. However, while the biological activities of LPS and lipopeptide were unaffected by protease treatment, proteinase-K abolished the bioactivity of flagellin (FIG. 7).

CONCLUSION

The results from these assays showed that several commonly consumed foods can contain large quantities of TLR-2, TLR-4 and TLR-5 stimulants, reaching up to 1.1 µg bacterial lipopeptides (BLP)-equivalent or 2.7 µg lipopolysaccharides (LPS)-equivalent per gramme of food. Although, to the inventor's knowledge, the measurement of TLR-2- or TLR5-stimulants in foodstuffs has not been attempted previously, the inventor's findings do support earlier demonstrations of high levels of endotoxin in some food stuffs using the LAL assay. However, it should be noted that the LAL-based assays used in these previous studies have low specificity and are likely to generate false positive results, thereby significantly overestimating the genuine TLR-4-stimulating potential of food-borne endotoxins.

It has been proposed that, in addition to microbial molecules, several molecules of eukaryotic origin (i.e. potentially endogenous to foodstuffs) may also stimulate TLR-2 or TLR-4 signalling. However, several lines of evidence suggest that the TLR-2 and TLR-4 stimulants detected in each foodstuff reflect molecules derived from microbial sources, rather than endogenous food-derived TLR-stimulating molecules. For example, in several cases, very similar foodstuffs (most notably the minced meats) contained abundant TLR-2 and TLR-4 stimulants while others of the same food type did not. Polymyxin-B also efficiently inhibited the TLR-4-signalling of each positive food extract, suggesting that LPS, and not endogenous food molecules, is the agent responsible for TLR-4-signalling in these extracts. The inventor has also showed recently that saturated fatty acids do not stimulate TLR-2 or TLR-4 signalling.

These findings therefore suggest that apparently unspoiled foodstuffs may nevertheless contain, at some point in their preparation or processing, a sufficient microbial load to release TLR-2 and TLR-4 stimulants into their growth environment. This notion is supported by many previous studies showing that certain commonly consumed foodstuffs can contain a high bacterial load before cooking, such as fresh beef mince which has often been shown to contain $\sim 10^5$-$10^7$ CFU/g bacteria. Notably, however, the purpose of this study was not to examine the microbial quality of each foodstuff, since PAMP biological activity is retained independently of bacterial viability or cooking. Further studies are therefore warranted to establish which types of food-borne micro-organism may represent the dominant contributors to PAMP contaminants in each type of food product.

Previous studies in mice suggest that ~0.2% of orally ingested radiolabelled LPS can be absorbed into the circulation when dietary fat is present to facilitate absorption, and such LPS was shown to retain its biological activity after translocation from the gut into the circulation. Remarkably, oral gavage of mice with as little as 39 µg of LPS results in systemic cytokine release, while higher doses of oral LPS re-activated both ovalbumin and collagen-induced arthritis in mice. If humans also absorb 0.2% of ingested LPS, these findings suggest that a meal containing 100 µg LPS could lead to the absorption of 200 ng LPS. By way of comparison, a bolus injection of 7 ng LPS results in marked systemic inflammation, including IL-6 and TNF-α release, in healthy human subjects.

In terms of potential for absorption of dietary lipopeptides, it is interesting to note that BLP has very similar physicochemical properties to LPS and could therefore also translocate via similar pathways. Indeed oral administration of synthetic lipopeptides was shown to result in systemic immune responses in mice. Thus, it is tempting to speculate that the occasional ingestion of meals high in LPS and/or BLP could promote transient, mild, systemic inflammatory episodes that predispose subjects to the development of atherosclerosis and insulin resistance. If future studies establish this to be the case, the potential health benefit of modifying food preparation protocols to minimise potential contamination with these agents may merit further investigation.

In conclusion, the present findings indicate that inflammatory stimulants of TLR-2, TLR-4 and TLR-5 can be present at levels of potential biological significance in many foodstuffs common to the Western diet. These contaminants may be of pathological relevance in the context of common chronic inflammatory diseases, such as atherosclerosis, insulin resistance and arthritis.

Example 2

Quantifying Stimulant Levels in a Meal

A representative sample of a meal is taken, including proportionally all constituent foodstuffs, of approximately 50 g, in the form likely to be ingested (e.g. cooked or uncooked). The meal is homogenised into 10 volumes (or similar) of phosphate buffered saline using a blender or similar. Aliquots of meal homogenate are centrifuged in 1.5 ml eppendorfs to pellet insoluble food items at 13,000 rpm for 5 minutes. The supernatants of centrifuged food extracts are sterile filtered. The sterile-filtered food extracts are diluted 1:10, or at greater dilutions, in tissue culture medium containing serum and applied to HEK-293 cells (or a similar cell-line that does not express endogenous TLRs) transfected with TLR2 or TLR4 and reporter constructs as described above.

The reporter assay is calibrated using a range of concentrations of lipopeptide and LPS standards (or other respective TLR/NOD stimulants) in the same plate used to measure food extracts.

Foodstuffs containing TLR4-stimulants with a biological activity greater than 100 ng LPS-equivalent per gramme food would be deemed to have potential to promote systemic inflammatory signalling in subjects consuming such a meal.

Foodstuffs containing TLR2-stimulants with a biological activity greater than 300 ng $Pam_3CSK_4$-equivalent per gramme food would be deemed to have potential to promote systemic inflammatory signalling in subjects consuming such a meal.

Subjects at risk of post-prandial inflammation may then be prescribed anti-inflammatory medications, such as ibuprofen or aspirin.

Example 3

Foodstuff Design

To reduce the oral endotoxin load for subjects at risk of insulin resistance and thereby reduce their risk of further impairment of insulin sensitivity, a typical diet for such subjects comprises the following advice:

Foodstuffs should be as fresh as possible.
All potential sources of spoiled meat, vegetables or dairy produce should be eliminated.
All minced meat based products that have been stored after mincing for any length of time should be avoided.
Intact fresh meat or fish products are acceptable.
Foods prepared from processed dairy products, such as chocolate and ice cream products, should be avoided.
Increase intake of unspoiled fruit and vegetables.
Reject items with blemishes associated with plant diseases.
Avoid processed products, such as ready meals, where it is not clear how or for how long ingredients may have been stored prior to processing.
The quantity of TLR-stimulants and/or NLR-stimulants in the foodstuff of the meal should be routinely assessed.

Example 4

Determining the type of PAMP in a Foodstuff

If a foodstuff is found to promote inflammation in human subjects, or in a simplified in vitro screen such as cultured macrophages, the type of PAMP responsible for promoting this inflammation may be determined using the following assay.

HEK-293 cells, or a similar TLR-deficient cell-line, transfected with NF-kB sensitive reporter and CD14 may be, in separate and parallel cultures, additionally co-transfected with TLR2, TLR4, TLR5, TLR9, NOD-1 or NOD-2. Positive activation of NF-kB reporter relative to cells cultured in medium alone indicates stimulation of the receptor transfected into each cell (provided that cells transfected with reporter and CD14 alone show no activation of reporter). In this way, the type of PAMP contaminant (i.e. lipopeptide, LPS or flagellin etc.) present in the foodstuff responsible for causing inflammation may be identified.

Identification of the type of stimulant present in foodstuffs responsible for promoting inflammation may then provide useful information that may be used to enable the identification and removal the source of the contaminant from the food preparation process, or specific therapeutics to neutralise the biological effects of the particular stimulant in vivo.

Example 5

The inventor next attempted to determine whether saliva contains any appreciable quantities of endotoxin, or other similar agents that may elicit an innate immune activation of human monocytes, and cause periodontitis, diabetes or cardiovascular disease. As with the previous examples, the inventor quantified the levels of stimulants of Toll-like receptor (TLR)-2, TLR-4 and TLR-5, but this time, in saliva samples, as opposed to food samples.

Materials and Methods
Ethics and Informed Consent

Subjects gave written informed consent for the study which was approved by the University of Leicester College of Medicine Research Ethics Committee and by the Glasgow Dental Hospital and School Ethics Committee. All subjects were also informed that they had the right to withdraw from the study at any time.

Recruitment of Subjects and Sample Collection

Saliva (~4 ml) was collected from 20 healthy human volunteers by expectoration into sterile universal tubes, not less than 30 minutes after eating or drinking Saliva samples from 20 age- and sex-matched patients with chronic adult periodontitis were also examined. Prospective patients were identified by screening the patient databanks of the Periodontal Department of Glasgow Dental Hospital and School for subjects who had presented for treatment with a Community Periodontal Index of Treatment Need (CPITN) score of 4 in at least one sextant and had then completed a course of periodontal treatment and were receiving supportive therapy as described earlier (Lappin et al. (2007) *Journal of Clinical Periodontology* 34, 271-277). Saliva samples were promptly stored at −20° C. and thawed immediately before analysis.

Inclusion Criteria

The subjects with chronic periodontitis had at least 16 teeth, including at least four molars, and had, in different quadrants, at least two periodontal pockets greater than 4 mm in depth, with a minimum of 2 mm attachment loss and reported brushing teeth at least twice daily.

Exclusion Criteria

Patients were excluded if they presented with any other periodontal condition or systemic disease (e.g. diabetes or cardiovascular disease, etc.), if they were pregnant; or if they had received antibiotic therapy within the past 3 months; or if they had taken non-steroidal anti-inflammatory drugs in the past 6 weeks. Smokers who smoked fewer than 10 cigarettes per day and former smokers, were also excluded.

Cell Culture and Reagents

Human embryonic kidney (HEK)-293 cells were cultured in DMEM supplemented with 10% foetal calf serum (FCS, Sigma). PAMP-standards for assay callibration were, for TLR2, synthetic bacterial lipopeptide $Pam_3CSK_4$ (Invivogen), for TLR4, *Escherichia coli* LPS repurified by phenol-water re-extraction to remove TLR2-stimulating lipopeptide contaminants as described previously (Hirschfeld et al. 2000, Journal of Immunology 165, 618-622), and for TLR5, *Salmonella typhimurium* flagellin (Invivogen). Oxidised palmitoyl arachidonyl phosphatidyl choline (OxPAPC) was prepared by auto-oxidation in air for 72 h as described previously (Erridge et al. 2008, Journal of Biological Chemistry 283, 24748-24759).

Quantification of TLR-Stimulants in Saliva Samples

TLR-stimulants were quantified in both whole heat-treated saliva (100° C. for 10 minutes), intended to reflect total bacteria-associated TLR-stimulants, and in saliva diluted 1:10 in PBS and filter-sterilised (0.22 μm, Acrodisc), intended to reflect soluble TLR-stimulants in human saliva. A recently developed bioassay based upon the measurement of NF-κB-dependent reporter activation in TLR-deficient HEK-293 cells transfected with human TLR2, TLR4/MD2 or TLR5, and calibrated with TLR2-, TLR4- or TLR5-stimulating standards (Erridge et al., 2010, Public Library of Science One 5, e9125), was used to quantify TLR-stimulants in saliva samples. Briefly, cells were plated in 96-well plates at $2 \times 10^4$ cells per well and transfected after 24 h using Genejuice (Novagen). Amounts of construct per well were 30 ng of human TLR2, TLR4 (co-expressing MD-2) or TLR5 (Invivogen), 30 ng of CD14 and 10 ng of firefly luciferase-reporter construct driven by the NF-κB dependent E-selectin promoter (pELAM). 3 days after transfection, cells were challenged in triplicate with heat-treated or sterile-filtered saliva samples diluted 1:100 in DMEM/1% FCS. In the same plate, an 8-point standard curve was prepared using dilutions of $Pam_3CSK_4$ (100 ng/ml to 0.032 ng/ml), *E. coli* LPS (100 ng/ml to 0.032 ng/ml) or *S. typhimurium* flagellin (from 1,000 ng/ml to 15 ng/ml), in duplicate. After 18 h, NF-κB-dependent reporter expression was measured using Promega Dual-Glo reagent. Fold induction of reporter was calculated relative to cells cultured in medium alone and a standard curve was prepared by plotting fold NF-κB induction vs concentration for each standard PAMP. The relative biological activities of specific TLR-stimulants in saliva were then calculated as ng per ml saliva, and are presented as a relative biological activity with respect to $Pam_3CSK_4$, LPS or flagellin, as described previously (Erridge et al. 2010 supra). For example, results presented as 200 ng/ml lipopeptide-equivalents indicate that 1 ml of saliva contains TLR2-stimulants with a capacity to stimulate TLR2-signalling equal to that of 200 ng $Pam_3CSK_4$. The coefficient of variance of the assay averaged ~20%. PAMP standards did not induce signalling in cells expressing heterologous TLRs, or in cells transfected with CD14 alone (Erridge et al. 2008 supra).

Bacterial Strains Used

Strains of bacteria examined were: *Aggregatibacter actinomycetemcomitans* (NCTC9709); *Campylobacter rectus* (DRWH); *Fusobacterium nucleatum* (NCTC10502); *Streptococcus sanguinis* (NCTC7163); *Streptococcus salivarius* (NCTC8018); *Tannerella forsythensis* (ATCC95137); *Lysobacter enzymogenes* (DSM 1895); *Porphyromonas gingivalis* (NCTC 11834); *Porphyromonas gingivalis* (W50); *Prevotella intermedia* (ATCC 25611); *Prevotella oris* (ATCC 33573); *Peptostreptococcus micros* (NCTC 11808); *Streptococcus mutans* (NCTC 10449); *Pseudomonas aeruginosa* (PAC 611) and *Escherichia coli* K12 (ATCC 27325). Each strain was resuspended in saline to an absorbance at 600 nm of 1.0, equivalent to $\sim 10^9$ bacteria/ml, and heat-killed at 100° C. for 10 minutes before storage at −20° C. prior to assay. The capacity of each organism to stimulate TLR2-, TLR4- or TLR5-dependent signalling at $10^7$ bacteria/ml was then measured in HEK-293 cells transfected as described above. Positive controls for NF-κB activation were 10 ng/ml *E. coli* LPS, 10 ng/ml $Pam_3CSK_4$ (Pam3), 10 ng/ml *S. typhimurium* flagellin (Flag) or 10 μg/ml polyinosinic acid (PolyI:C) which stimulates NF-κB activation independently of TLR2, TLR4 or TLR5 in HEK-293 cells (Erridge et al. 2008). Results are reported as mean fold-induction of NF-κB reporter in triplicate cultures relative to cells cultured in medium alone.

Growth of *E. coli* for Measurement of TLR-Stimulants in Conditioned Media

In order to investigate the extent of shedding of soluble TLR2- and TLR4-stimulants by a model enterobacterial organism, cultures of *E. coli* K12 were grown in luria broth (LB) from a starting density of $\sim 1 \times 10^8$ bacteria/ml with shaking at 37° C. 1 ml aliquots were taken each hour for 4 hours and optical density (OD) at 600 nm was measured to provide an estimate of bacterial growth (OD of 1.0 was assumed to reflect $\sim 10^9$ bacteria/ml). Aliquots taken at each time-point were centrifuged (13,000 g for 5 mins), and the supernatant was filter-sterilised (0.22 μm, Acrodisc). Soluble TLR2- and TLR4-stimulants were then measured in each supernatant by bioassay as described above.

Statistics

Log 10-transformation of TLR-stimulant concentrations was performed to normalise the data distribution before analysis. Transformed TLR-stimulant concentrations in saliva of healthy and periodontitis subjects were then compared using the Student's T-test. ANOVA with Dunnett's or Tukeys post-test was used to compare TLR-dependent NF-κB activation induced by defined bacterial isolates, or saliva samples treated with TLR-inhibitors, respectively. For comparison of TLR-stimulant levels between high and low responders, values were log-transformed and means of the pooled results from the 3 days examined were compared by Student's T-test. Pearson's $r^2$ was used to measure correlation between variables. Differences were considered statistically significant at $P<0.05$.

Results

Clinical Data

The periodontitis patients (age 41+/−2.5 years, 13F:7M, 8 smokers) brushed at least twice daily, had a mean pocket depth of 2.84 (±0.37) mm, number of teeth was 24.1 (±1.6), number of sites with pocket depth>4 mm was 12.0 (±10.4) and clinical attachment level was 3.53 (±0.75) mm. As a measure of gingival inflammation, bleeding on probing was recorded within the patient group. This analysis revealed that on average 30% (+/−10%) of sites bled on probing. All the healthy controls (age 38+/−10.7 years, 14F: 6M, 2 smokers) had between 27 and 32 teeth (where orthodontic reasons accounted for missing teeth), had no history of periodontitis, reported no bleeding of gums on toothbrushing, and brushed on average 1.9 times per day. All clinical data are presented as means+/−SD.

Quantification of TLR-Stimulants in Heat-Sterilised Human Saliva

TLR-stimulant concentrations in saliva samples were measured in two ways. First, saliva samples were heat-sterilised to represent the total PAMP content present in saliva, including those attached to bacteria. Next, saliva diluted 1:10 in PBS was filter-sterilised to yield an extract intended to reflect the soluble PAMPs present in saliva. These two preparations were investigated separately as it was reasoned that soluble PAMPs may be more likely to be absorbed than PAMPs that remain attached to bacteria (Ghoshal et al. 2009, Journal of Lipid Research 50, 90-97).

Figure 8:
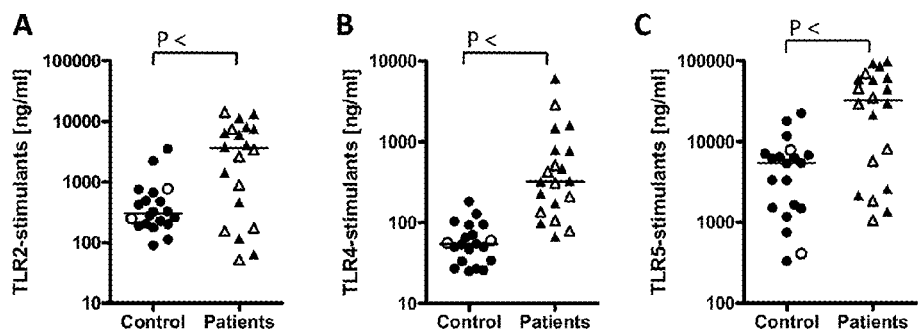
FIG. 8 shows the quantification of TLR-stimulants in heat-treated saliva. The biological activities of total stimulants of TLR2 (A), TLR4 (B) and TLR5 (C) were quantified relative to $Pam_3CSK_4$, *E. coli* LPS and *S. typhimurium* flagellin standards, using TLR-transfected HEK-293 cells as described in the materials and methods, in heat-treated saliva from healthy subjects (n=20) and periodontitis patients (n=20). Open symbols represent smokers.

In heat-treated saliva of healthy subjects, median TLR2-stimulant concentrations were 304 ng/ml (range 90 to 3,540 ng/ml) lipopeptide-equivalents, as measured relative to the biological activity of $Pam_3CSK_4$ synthetic lipopeptide standard. The results are shown in FIG. 8. FIG. 8A shows that median TLR2-stimulants were 3,640 ng/ml (range 52 to 14,300 ng/ml) lipopeptide-equivalents in saliva from periodontitis patients ($P<0.01$ vs healthy subjects). FIG. 8B shows that median TLR4-stimulants measured in heat-treated saliva from healthy subjects were 55 ng/ml (range 25 to 182 ng/ml), as measured relative to the biological activity of *E. coli* LPS standard, and 325 ng/ml (range 67 to 6,090 ng/ml) in saliva from periodontitis patients ($P<0.001$ vs control saliva). As shown in FIG. 8C, median TLR5-stimulants were 5.4 μg/ml (range 0.3-23 μg/ml) in healthy subjects and 32 μg/ml (range 1.1-98 μg/ml), relative to *S. typhimurium* flagellin, in periodontitis patients ($P<0.001$ vs control saliva).

Quantification of Soluble TLR-Stimulants in Filter-Sterilised Human Saliva

With reference to FIG. 9, the inventor next quantified the abundance of soluble stimulants of TLR2, TLR4 and TLR5 in filter-sterilised saliva. As shown in FIG. 9A, median soluble TLR2 stimulants were 77 ng/ml (range 24-465 ng/ml) in healthy subjects and 3,450 ng/ml (range 44-35,100 ng/ml) in periodontitis patients ($P<0.001$). Referring to FIG. 9B, median soluble TLR4-stimulants were 7 ng/ml (range 4-99 ng/ml) in healthy subjects and 138 ng/ml (range 77-2,020 ng/ml) in periodontitis patients ($P<0.001$). Soluble TLR5-stimulants were not detectable in the sterile-filtered saliva samples, suggesting that flagellin may remain predominantly attached to bacteria or in the multimeric form rather than existing in the soluble form in human saliva. Levels of TLR2-stimulants correlated with levels of TLR4-stimulants in both the insoluble fraction ($R^2=0.7136$, $P<0.001$) and the soluble fraction ($R^2=0.8501$, $P<0.001$). There were no significant differences in PAMP concentrations between smokers and non-smokers and there was no correlation between number of sites of pocket depth>4 mm, or age and PAMP concentrations.

Daily Variation in TLR-Stimulant Concentrations in Human Saliva

Figure 10:
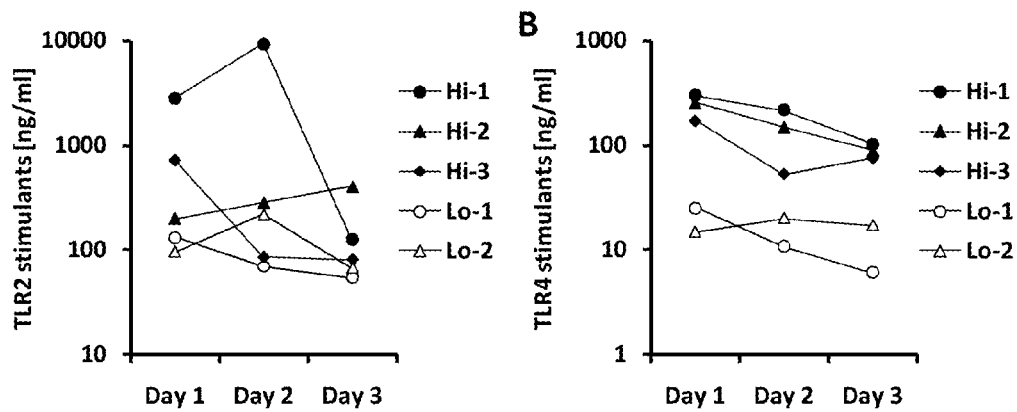
FIG. 10 shows daily variation in TLR2- and TLR4-stimulants in human saliva. The biological activities of soluble stimulants of TLR2 (A) and TLR4 (B) were quantified in filter-sterilised saliva from 3 healthy subjects with elevated TLR4-stimulants and 2 healthy subjects with normal levels of TLR4-stimulants on 3 separate days within a 5 day period.

With reference to FIG. 10, in order to examine the stability of oral PAMP profile with time, 3 healthy subjects with the highest oral TLR4-stimulants, and 2 healthy subjects with average levels of oral TLR4-stimulants, were asked to provide further saliva samples on three separate days within a five day period approximately two months after the initial sampling. Referring to FIG. 10A, median lipopeptide levels of the chosen low and high responders were 29 vs 369 ng/ml, respectively, at the first timepoint, and 82 vs 281 ng/ml over the 3 s tested 2 months later. Median LPS levels were 7 vs 42 ng/ml at the first timepoint, and 16 vs 149 ng/ml in the same subjects 2 months later. As shown in FIG. 10B, oral TLR4-stimulant levels were significantly higher in high responders than in low responders when pooled data from the 3 days examined were compared ($P<0.001$), indicating that oral TLR4-stimulants may be relatively stable with time. A similar, although weaker, trend was observed with respect to oral TLR2-stimulants over the 3 days examined ($P=0.051$).

Molecular Characterisation of TLR2 and TLR4 Stimulants in Human Saliva

Figure 11:
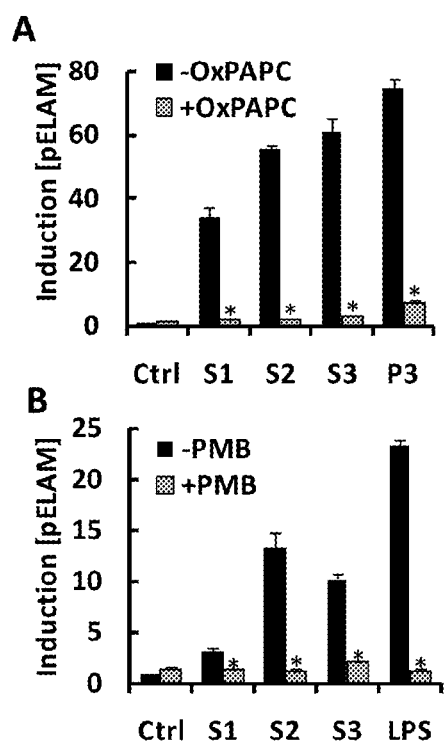
FIG. 11 shows the effect of lipopeptide and LPS inhibitors on oral TLR-stimulant signalling. Filter-sterilised saliva from 3 patients was diluted 1:100 in tissue culture medium and applied to HEK-293 cells transfected with TLR2 (A) or TLR4/MD2 (B) in the presence or absence of 25 µg/ml OxPAPC (an inhibitor of bacterial lipopeptide signalling) or 10 µg/ml polymyxin-B (PMB, an inhibitor or LPS-signalling). Fold induction of NF-κB sensitive reporter (pELAM) was measured relative to cells cultured in medium alone after 18 h. Positive controls were 10 ng/ml $Pam_3CSK_4$ (P3) or *E. coli* LPS. *P<0.05.

As a variety of molecules of diverse origin and structure have been proposed to stimulate TLR2 or TLR4 (Kumar et al. 2009, Biochemical and Biophysical Research Communications 388, 621-625), the inventor aimed to establish which class of molecule may be responsible for stimulating TLR2 and TLR4 signalling in human saliva, and the results are shown in FIG. 11. As shown in FIG. 11A, a specific inhibitor of bacterial lipopeptide signalling, OxPAPC, which was shown previously to inhibit lipopeptide signalling but not general downstream TLR- or cytokine-signalling components, significantly blocked TLR2-dependent signalling induced by patient saliva samples. As shown in FIG. 11B, polymyxin-B, an agent which binds and neutralises LPS, significantly inhibited TLR4-signalling induced by patient saliva samples. These data suggest that the majority of the TLR2 and TLR4 stimulants present in human saliva are bacterial lipopeptides, and LPSs, respectively.

TLR-Stimulation by Cultured Oral Bacteria

Figure 12:
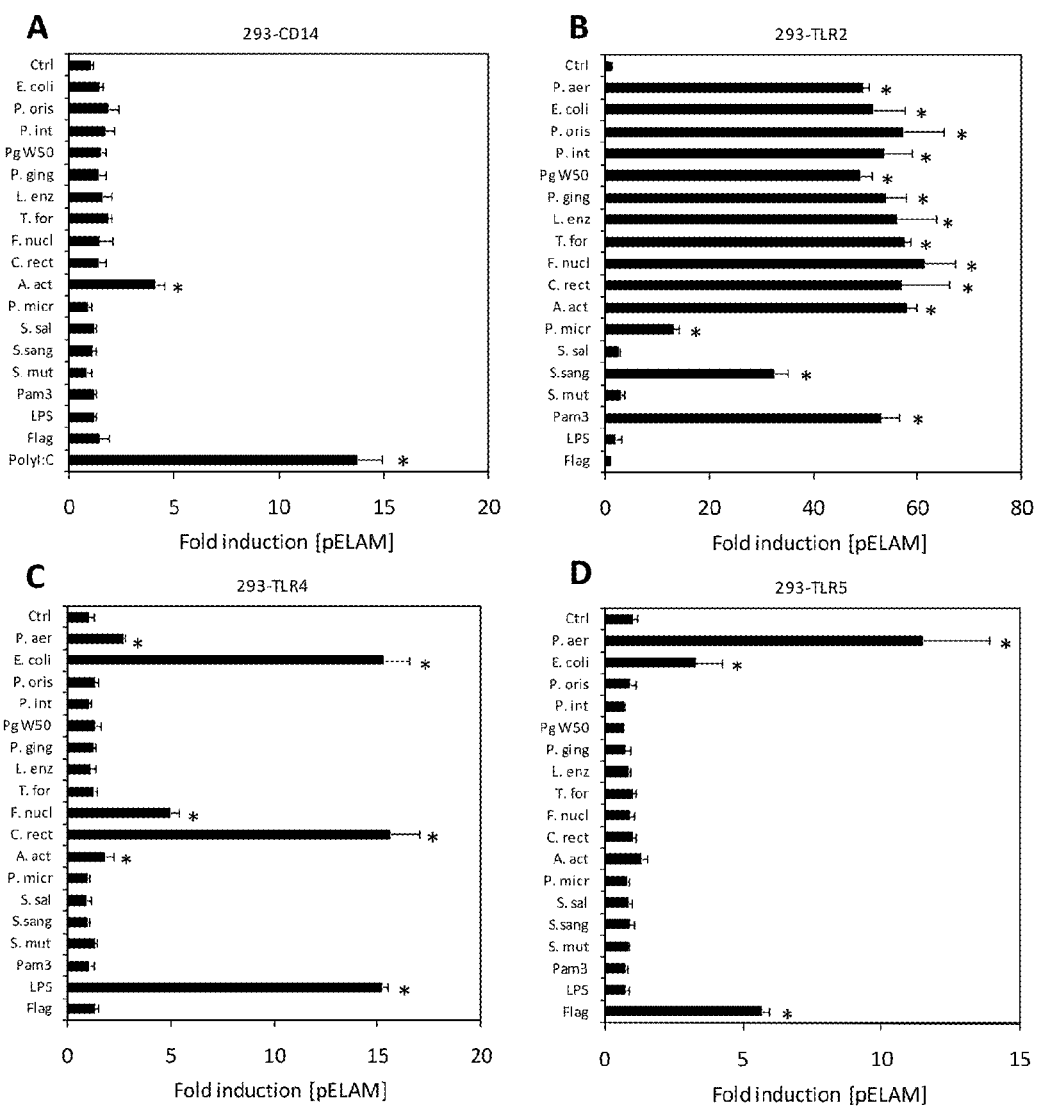
FIG. 12 shows the capacity of defined oral bacterial isolates to stimulate TLR2, TLR4 and TLR5-signalling. Defined cultures of oral bacteria were heat-killed and applied at a concentration of $10^7$ bacteria/ml to HEK-293 cells transfected with CD14(A), TLR2 (B), TLR4/MD2 (C) or TLR5 (D) and NF-κB-dependent reporter (pELAM). Positive controls for NF-κB activation were 10 ng/ml *E. coli* LPS, 10 ng/ml $Pam_3CSK_4$ (Pam3), 10 ng/ml *S. typhimurium* flagellin (Flag) or 10 µg/ml polyinosinic acid (PolyI:C). Mean fold induction of NF-κB reporter from triplicate cultures relative to cells cultured in medium alone (Ctrl) is shown +/−SD. Results are representative of at least 3 experiments.

In order to identify potential bacterial contributors to the pools of TLR-stimulants in saliva, the inventor next examined a panel of common oral micro-organisms in terms of their potential to stimulate TLR-signalling in transfected HEK-293 cells, and the results are shown in FIG. 12. As expected, referring to FIG. 12A, HEK-293 cells were insensitive to most bacteria in the absence of TLR-co-transfection. Surprisingly, however, a modest but significant TLR-independent activation of NF-κB signalling was reproducibly observed in response to *A. actinomycetemcomitans*. Although most of the isolates stimulated TLR2-dependent signalling as expected, several *streptococcus* species stimulated only a weak or not-detectable TLR2-dependent signal, even when re-examined at higher concentrations, as shown in FIG. 12B. The Gram-negative oral organisms *C. rectus, A. actinomycetemcomitans* and *F. nucleatum* stimulated TLR4-dependent signalling, while *T. forsythensis, L. enzymogenes, P. intermedia, P. oris* and two strains of *P. gingivalis* did not (see FIG. 12C). TLR5 signalling was induced only by the flagellated organisms *E. coli* and *P. aeruginosa*, as shown in FIG. 5D.

Shedding of TLR2- and TLR4-Stimulants by *E. coli*

Figure 13:
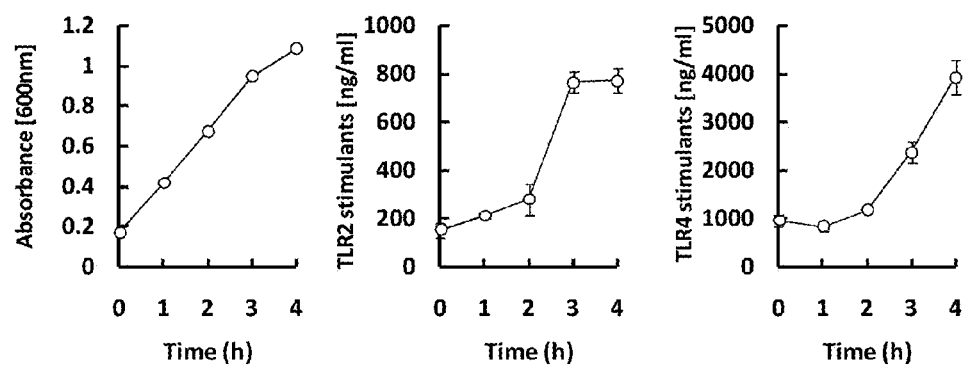
FIG. 13 shows the quantification of TLR2- and TLR4-stimulants in log-phase *E. coli* growth medium. *E. coli* K12 cultures grown in LB at 37° C. for 4 h were monitored hourly for absorbance at 600 nm (A), biological activity of soluble TLR2-stimulants in growth medium (B) and biological activity of soluble TLR4-stimulants in growth medium (C). Results shown are means of triplicate measurements+/− SD and are representative of at least 3 experiments.

Finally, the inventor aimed to establish the normal range of TLR2- and TLR4-stimulants shed by a model enterobacterial organism, *E. coli* K12, under log-phase growth conditions, and the results are shown in FIG. 13. Quantification of the soluble PAMPs in growth supernatant from cultured *E. coli* K12 revealed a linear relationship between bacterial cell numbers and concentrations of soluble TLR2- and TLR4-stimulants ($R^2=0.867$ and $0.755$, respectively). Calculation of the ratios between lipopeptide- or LPS-equivalents and bacterial cell concentrations revealed that soluble LPS-equivalents averaged 3.1 ng per $10^6$ bacteria and soluble lipopeptide-equivalents averaged 0.7 ng per $10^6$ bacteria.

Discussion

The present study identified that median levels of soluble TLR2- and TLR4-stimulants were around 80 ng/ml and 7 ng/ml, respectively, in the saliva of healthy subjects, while soluble TLR2- and TLR4-stimulants were approximately 20- and 50-fold more abundant in saliva of periodontitis patients, respectively (see FIG. 9). The inventor's aim was to measure the relative biological activity of TLR-stimulants in saliva, and they found that the LAL assay was not suitable for this purpose for several reasons. First, the endotoxins of a number of Gram-negative oral organisms have been shown to be antagonists, rather than agonists, of human TLR4 (Coats et al. 2003, Infection and Immunity 71, 6799-6807; Kikkert et al. 2007, Oral Microbiology and Immunology 22, 145-151; Yoshimura et al. 2002, Infection and Immunity 70, 218-225), while these endotoxins may stimulate a positive reaction in the limulus assay (Erridge et al. 2007, *Cardiovascular Research* 73, 181-189). Next, as the limulus assay is based upon components of the innate immune system of the horseshoe crab, interspecies receptor differences may lead to inaccurate estimation of the pro-inflammatory potential of endotoxins in human systems. The over-estimation of the endotoxin content of saliva by the LAL assay in earlier studies likely reflects these issues, although the inventor's findings confirm the earlier observation that endotoxin levels in saliva tend to remain relatively stable with time in healthy subjects (Leenstra et al. 1996, Oral Surgery, Oral Medicine, Oral Pathology, Oral Radiology and Endodontics 82, 637-643). Finally, the limulus assay is not capable of detecting lipopeptides or flagellins and therefore cannot be used for their quantification (Erridge & Samani, 2009, Arteriosclerosis Thrombosis and Vascular Biology 29, 1944-1949).

In order to overcome these difficulties, a bioassay-based approach using receptors of the human innate immune system was developed to quantify the abundance of TLR-stimulants in human saliva. This approach revealed that stimulants of TLR2, TLR4 and TLR5 are present at surprisingly higher concentrations in saliva of periodontitis patients than in saliva of healthy subjects. Previous studies suggest that the observed differences are also not likely to be due to increased total bacterial load in saliva of periodontitis patients, as total bacterial counts have been reported to be similar in saliva of subjects with gingivitis, periodontitis and good periodontal health.

Instead, although not wishing to be bound by theory, the inventor believes that an alternative explanation may lie in the well-established shift in the oral microflora balance towards Gram-negative organisms in periodontitis. The inventor has shown that Gram-negative organisms generally secrete ~100-1,000-fold more soluble TLR2-stimulants than Gram-positive organisms (Erridge et al. 2010 supra). Thus, expansion of the sub-gingival Gram-negative microflora may lead to an increased shedding of soluble TLR-stimulants in the mouth which may be detected in saliva. TLR2-stimulants may also have the potential to promote periodontitis, as it was shown that TLR2-deficient mice are resistant to bone-loss in a *P. gingivalis* mediated model of periodontitis.

The inventor found that six strains of oral Gram-negative bacteria from a panel of nine examined did not stimulate TLR4-dependent signalling (see FIG. 12). These results further exemplify the advantage of the assay over the limulus assay for measurement of bacterial endotoxins in biological samples, as the limulus assay would falsely identify endotoxins of these organisms as contributing to inflammatory risk.

It has been proposed that products of the oral microbiota may contribute to the development of atherosclerosis and insulin resistance (Beck et al. 2001, Arteriosclerosis Thrombosis and Vascular Biology 21:1816-1822; Teeuw et al. 2010, Diabetes Care 33:421-427; Tonetti 2009, Journal of Clinical Periodontology 36 Suppl 10:15-19). Traditionally, it has been assumed that the mechanisms underlying these observed associations involve transient endotoxaemias and bacteraemias induced by tooth brushing or chewing. However, the inventor believes that bacterial products present in the small intestine may be absorbed with dietary fat to promote low-grade systemic inflammation, thereby potentiating these diseases. As LPS and lipopeptide retain biological activity following protease-treatment or low pH, it is possible that swallowed products of the oral microflora may survive passage through the stomach to contribute to the biologically active pools of TLR-stimulants in the small intestine. The present findings therefore suggest that if healthy subjects swallow approximately one liter of saliva per day, ~7 μg LPS and ~80 μg lipopeptide may also be ingested each day.

By comparison with the oral microflora, the endogenous microflora of the small intestine is relatively limited, being generally <$10^2$ CFU/ml in the duodenum, $10^0$-$10^4$ CFU/ml in the jejunum, $10^3$-$10^6$ CFU/ml in the proximal ileum and $10^5$-$10^8$ CFU/ml in the most distal section of the ileum. However, Gram-negative organisms are rare in the small intestine and represent only a small fraction of these numbers. Thus, in health, it is likely that enterobacterial species, which have been shown to represent the major contributors to the endogenous soluble TLR2- or TLR4-stimulants in the small intestine, rarely exceed $10^5$ organisms/ml. The results presented in FIG. 13 therefore suggest that the maximum concentration of LPS or lipopeptide derived from the resident microflora of the small intestine is likely to be around 0.3 ng/ml LPS and 0.1 ng/ml lipopeptide. These preliminary estimates therefore suggest for the first time that under most conditions the TLR2- and TLR4-stimulants present in the small intestine are likely to derive largely from the oral microflora, rather than from the indigenous microflora of the small intestine.

In summary, the inventor has demonstrated for the first time that periodontal disease is associated with marked increases in salivary concentrations of stimulants of TLR2 and TLR4, relative to healthy subjects. The inventor also believes that periodontitis may increase the risk of developing diseases such as atherosclerosis and insulin resistance via mechanisms that involve the stimulation of chronic inflammatory signalling pathways caused by elevated levels of TLR-stimulants derived from the oral microbiota.

Example 6

To determine whether or not endotoxin (LPS, lipopolysaccharide), delivered by the oral route, is capable of modulating inflammatory events systemically, mice were given a bolus dose of LPS, or vehicle, by the oral route and mRNA expression of inflammatory markers (ICAM-1 and VCAM-1) was measured in heart tissue after 48 h.

Specifically, C57/BL6 mice were challenged with 0.2 ml phosphate buffered saline (PBS, to serve as negative control animals receiving no inflammatory stimulus) or 0.2 ml PBS containing 1 mg *Escherichia coli* LPS by oral gavage (n=6 per group). Animals were sacrificed at 48 h, RNA was then extracted from heart tissue and converted to cDNA for real-time PCR analysis of genes involved in inflammatory signalling.

As shown in FIGS. 14 and 15, mice treated with LPS showed a ~3-fold increase in expression of intercellular adhesion molecule (ICAM-1) and a ~7-fold increase in expression of vascular cell adhesion molecule (VCAM-1). Both of these molecules are key mediators of inflammation in the vasculature and play a central role in the progression of atherosclerosis and other inflammatory diseases. These results therefore confirm that LPS delivered by the oral route can result in increases in inflammatory markers systemically.

Because mice are ~250-fold less sensitive to endotoxin than human subjects (Copeland et al. Clin Diagn Lab Immunol 2005), the dose of orally administered LPS in these experiments (~50 mg per kg body weight) should be equivalent to a dose of ~0.2 mg per kg body weight in human subjects. Assuming an average body weight of 70 kg, this is equivalent to a bolus dose of 14 mg in humans. Published studies have shown that this level of exposure could conceivably be encountered at least occasionally among subjects consuming the Western diet (Erridge C, Br J Nutr, 2010; Erridge C, J Food Sci 2011; Erridge C, Food Chem Toxicol 2011).

The invention claimed is:

1. A method for measuring the concentration of inflammatory molecules in an orally-ingestible biological sample comprising:
   (i) treating an orally-ingestible biological sample to remove or kill live bacteria;
   (ii) contacting the treated sample of (i) with means for determining the concentration of a Toll-like receptor 2 (TLR-2)-stimulant, a Toll-like receptor 4 (TLR-4)-stimulant or a Toll-like receptor 5 (TLR-5)-stimulant by biological activity; and
   (iii) determining the concentration of the TLR-2, TLR-4 or TLR-5-stimulant in the treated sample, wherein: (a) the concentration of the TLR-stimulant is determined by comparing its biological activity with respect to a known stimulant of TLR, (b) the known stimulant of TLR is lipopolysaccharide (LPS), bacterial lipopeptides (BLP) or flagellin, and (c) the TLR-2, TLR-4 or TLR-5-stimulant is the inflammatory molecule, and
   wherein the means for determining the concentration of a TLR-stimulant by biological activity comprise a cell that does not normally express TLRs and that is transfected with TLR-2, TLR-4, and/or TLR-5.

2. A method according to claim 1, wherein the orally-ingestible biological sample comprises saliva or a foodstuff.

3. A method according to claim 1, wherein (i) the lipopolysaccharide (LPS) is derived from enterobacterial species, pseudomonad species, *acinetobacter* species or *erwinia* species, or (ii) wherein the bacterial lipopeptide (BLP) is a di-acyl-lipopeptide derived from spirochetes or *mycoplasma* species, or a tri-acyl lipopeptide derived from Gram-positive and Gram-negative bacteria, or (iii) wherein the flagellin is expressed by any motile bacteria selected from the group consisting of any enterobacterial species, *Salmonella typhimurium*, pseudomonads, and *Pseudomonas putida*.

4. A method according to claim 1, wherein the concentration of the TLR-stimulant is determined by measuring the amount of secretion of pro-inflammatory cytokines or chemokines, and the pro-inflammatory cytokine is IL-1, IL-6, IL-12, IL-15, IL-18 and/or TNF-α, and the chemokine is IL-8 or MCP-1.

5. A method according to claim 1, wherein the concentration of the TLR-stimulant is determined by measuring the amount of NF-κB activity, and wherein NF-κB activity is measured by a reporter system selected from the group consisting of a reporter system activated by NF-κB and a bioluminescent reporter system based upon the reaction of luciferase and luciferin.

6. The method of claim 1, wherein the method comprises determining the concentration of at least two TLR-stimulants.

7. A method of monitoring a subject's diet for risk of containing molecules that promote inflammation, the method comprising:
   (i) treating at least one test foodstuff of a subject's meal to remove or kill live bacteria;
   (ii) contacting the treated foodstuff of (i) with means for determining the concentration of a Toll-like receptor 2 (TLR-2)-stimulant, a Toll-like receptor 4 (TLR-4)-stimulant or a Toll-like receptor 5 (TLR-5)-stimulant by biological activity; and
   (iii) determining the concentration of the TLR-stimulant in the treated foodstuff, wherein: (a) the concentration of the TLR-stimulant is determined by comparing its biological activity with respect to a known stimulant of TLR, (b) the known stimulant of TLR is lipopolysaccharide (LPS), bacterial lipopeptides (BLP) or flagellin, and (c) the TLR-2, TLR-4 or TLR-5-stimulant is the molecule that promotes inflammation, and
   wherein the means for determining the concentration of a TLR-stimulant by biological activity comprise a cell that does not normally express TLRs and that is transfected with TLR-2, TLR-4, and/or TLR-5.

8. A method for determining, in a foodstuff, the identity of a Toll-like receptor (TLR)-stimulant which causes inflammation, the method comprising:
   (i) treating the foodstuff to remove or kill live bacteria; and
   (ii) contacting the treated foodstuff of (i) with means for determining the presence of a TLR-2-stimulant, a TLR-4-stimulant or a TLR-5-stimulant by biological activity, wherein: (a) the presence of the TLR-stimulant is determined by comparing its biological activity with respect to a known stimulant of TLR, and (b) the known stimulant of TLR is lipopolysaccharide (LPS), bacterial lipopeptides (BLP) or flagellin, and
   wherein the means for determining the presence of a TLR-stimulant by biological activity comprise a cell that does not normally express TLRs and that is transfected with TLR-2, TLR-4, and/or TLR-5.

9. A method for determining the content of molecules that promote inflammation in an orally-ingestible biological sample, comprising:
   (i) contacting an orally-ingestible biological sample with means for determining the concentration of a Toll-like receptor 2 (TLR-2)-stimulant, a Toll-like receptor 4 (TLR-4)-stimulant, and a Toll-like receptor 5 (TLR-5)-stimulant by biological activity; and
   (ii) determining the concentration of the TLR-stimulants in the sample, wherein: (a) the concentration of the TLR-stimulants is determined by comparing biological activities with respect to known stimulants of TLR, (b) the known stimulants of TLR are lipopolysaccharide (LPS), bacterial lipopeptides (BLP), and flagellin, and (c) the TLR-2, TLR-4, and TLR-5-stimulants are the molecules the promote inflammation, and
   wherein the means for determining the concentration of a TLR-stimulant by biological activity comprise a cell that does not normally express TLRs and that is transfected with TLR-2, TLR-4, and/or TLR-5.

* * * * *